United States Patent
Moshe et al.

(10) Patent No.: US 8,753,335 B2
(45) Date of Patent: Jun. 17, 2014

(54) THERAPEUTIC ENERGY DELIVERY DEVICE WITH ROTATIONAL MECHANISM

(75) Inventors: Meir H. Moshe, El Sobrante, CA (US); Valerie L. Douglass, Sunnyvale, CA (US); Kevin L. Moss, Tracy, CA (US); Robert M. Pearson, San Jose, CA (US)

(73) Assignee: AngioDynamics, Inc., Latham, NY (US)

( * ) Notice: Subject to any disclaimer, the term of this patent is extended or adjusted under 35 U.S.C. 154(b) by 903 days.

(21) Appl. No.: 12/693,234

(22) Filed: Jan. 25, 2010

(65) Prior Publication Data

US 2010/0191235 A1  Jul. 29, 2010

Related U.S. Application Data

(60) Provisional application No. 61/146,984, filed on Jan. 23, 2009.

(51) Int. Cl.
*A61B 18/14* (2006.01)

(52) U.S. Cl.
USPC ............................................. 606/41; 606/49

(58) Field of Classification Search
USPC ...................................... 606/41–52
See application file for complete search history.

(56) References Cited

U.S. PATENT DOCUMENTS

| | | | |
|---|---|---|---|
| 1,653,819 A | 12/1927 | Northcott et al. | |
| 4,016,886 A | 4/1977 | Doss | |
| 4,226,246 A | 10/1980 | Fragnet | |
| 4,262,672 A | 4/1981 | Kief | |
| 4,407,943 A | 10/1983 | Cole et al. | |
| 4,810,963 A | 3/1989 | Blake-Coleman et al. | |
| 4,907,601 A | 3/1990 | Frick | |
| 4,946,793 A | 8/1990 | Marshall, III | |
| 5,019,034 A | 5/1991 | Weaver et al. | |
| 5,052,391 A | 10/1991 | Silberstone et al. | |
| 5,058,605 A | 10/1991 | Slovak | |

(Continued)

FOREIGN PATENT DOCUMENTS

| | | |
|---|---|---|
| EP | 0378132 | 7/1990 |
| WO | 9639531 | 12/1996 |

(Continued)

OTHER PUBLICATIONS

Amasha, et al., Quantitative Assessment of Impedance Tomography for Temperature Measurements in Microwave Hyperthermia, *Clin. Phys. Physiol. Meas.*, 1998, Suppl. A, 49-53.

(Continued)

*Primary Examiner* — Linda Dvorak
*Assistant Examiner* — Jocelyn D Ram
(74) *Attorney, Agent, or Firm* — Peter J. Flora

(57) ABSTRACT

A device for delivering therapeutic energy to tissue is provided. The device includes a housing and a rotating device coupled to the housing. The device includes a plurality of electrodes, each electrode including: (i) a proximal section longitudinally extending from within the housing to an exterior of the housing and having a longitudinal axis; (ii) an intermediate section extending from the proximal section; and (iii) a distal section extending longitudinally from the intermediate section. The rotating device is coupled to the proximal sections of the plurality of electrodes and adapted to rotate the distal section of the electrodes so that distance between at least two electrodes changes, so that the electrodes can be placed in a compact configuration or an expanded configuration to provide for a treatment region larger than the size of the opening for insertion.

14 Claims, 19 Drawing Sheets

(56) References Cited

U.S. PATENT DOCUMENTS

| | | |
|---|---|---|
| 5,098,843 A | 3/1992 | Calvin |
| 5,134,070 A | 7/1992 | Casnig |
| 5,173,158 A | 12/1992 | Schmukler |
| 5,193,537 A | 3/1993 | Freeman |
| 5,273,525 A | 12/1993 | Hofmann |
| 5,283,194 A | 2/1994 | Schmukler |
| 5,318,563 A | 6/1994 | Malis et al. |
| 5,328,451 A | 7/1994 | Davis et al. |
| 5,389,069 A | 2/1995 | Weaver |
| 5,403,311 A | 4/1995 | Abele et al. |
| 5,425,752 A | 6/1995 | Vu'Nguyen |
| 5,439,440 A | 8/1995 | Hofmann |
| 5,458,625 A | 10/1995 | Kendall |
| 5,533,999 A | 7/1996 | Hood et al. |
| 5,536,240 A | 7/1996 | Edwards et al. |
| 5,575,811 A | 11/1996 | Reid et al. |
| 5,626,146 A | 5/1997 | Barber et al. |
| 5,634,899 A | 6/1997 | Shapland et al. |
| 5,674,267 A | 10/1997 | Mir et al. |
| 5,702,359 A | 12/1997 | Hofmann |
| 5,720,921 A | 2/1998 | Meserol |
| 5,778,894 A | 7/1998 | Dorogi et al. |
| 5,782,882 A | 7/1998 | Lerman et al. |
| 5,800,378 A | 9/1998 | Edwards et al. |
| 5,810,762 A | 9/1998 | Hofmann |
| 5,836,905 A | 11/1998 | Lemelson et al. |
| 5,843,026 A | 12/1998 | Edwards et al. |
| 5,873,849 A | 2/1999 | Bernard |
| 5,919,142 A | 7/1999 | Boone et al. |
| 5,947,889 A | 9/1999 | Hehrlein |
| 5,983,131 A | 11/1999 | Weaver et al. |
| 5,991,697 A | 11/1999 | Nelson et al. |
| 5,999,847 A | 12/1999 | Elstrom |
| 6,009,347 A | 12/1999 | Hofmann |
| 6,010,613 A | 1/2000 | Walters et al. |
| 6,016,452 A | 1/2000 | Kasevich |
| 6,041,252 A | 3/2000 | Walker et al. |
| 6,055,453 A | 4/2000 | Hofmann et al. |
| 6,068,650 A | 5/2000 | Nanda et al. |
| 6,085,115 A | 7/2000 | Weaver et al. |
| 6,090,106 A | 7/2000 | Goble et al. |
| 6,102,885 A | 8/2000 | Bass |
| 6,106,521 A | 8/2000 | Blewett et al. |
| 6,109,270 A | 8/2000 | Mah et al. |
| 6,122,599 A | 9/2000 | Mehta |
| 6,132,419 A | 10/2000 | Hofmann |
| 6,159,163 A | 12/2000 | Strauss et al. |
| 6,208,893 B1 | 3/2001 | Hofmann |
| 6,210,402 B1 | 4/2001 | Olsen et al. |
| 6,212,433 B1 | 4/2001 | Behl |
| 6,216,034 B1 | 4/2001 | Hofmann |
| 6,219,577 B1 | 4/2001 | Brown et al. |
| 6,241,702 B1 | 6/2001 | Lundquist et al. |
| 6,261,831 B1 | 7/2001 | Agee |
| 6,278,895 B1 | 8/2001 | Bernard |
| 6,300,108 B1 | 10/2001 | Rubinsky |
| 6,326,177 B1 | 12/2001 | Schoenbach et al. |
| 6,347,247 B1 | 2/2002 | Dev et al. |
| 6,349,233 B1 | 2/2002 | Adams |
| 6,351,674 B2 | 2/2002 | Silverstone |
| 6,387,671 B1 | 5/2002 | Rubinsky et al. |
| 6,403,348 B1 | 6/2002 | Rubinsky et al. |
| 6,470,211 B1 | 10/2002 | Ideker et al. |
| 6,482,619 B1 | 11/2002 | Rubinsky et al. |
| 6,493,592 B1 | 12/2002 | Leonard et al. |
| 6,500,173 B2 | 12/2002 | Underwood et al. |
| 6,526,320 B2 | 2/2003 | Mitchell |
| 6,562,604 B2 | 5/2003 | Rubinsky et al. |
| 6,607,529 B1 | 8/2003 | Jones et al. |
| 6,611,706 B2 | 8/2003 | Avrahami et al. |
| 6,613,211 B1 | 9/2003 | McCormick et al. |
| 6,627,421 B1 | 9/2003 | Unger et al. |
| 6,653,091 B1 | 11/2003 | Dunn et al. |
| 6,669,691 B1 | 12/2003 | Taimisto |
| 6,692,493 B2 | 2/2004 | McGovern et al. |
| 6,697,669 B2 | 2/2004 | Dev et al. |
| 6,697,670 B2 | 2/2004 | Chornenky et al. |
| 6,702,808 B1 | 3/2004 | Kreindel |
| 6,795,728 B2 | 9/2004 | Chornenky et al. |
| 6,801,804 B2 | 10/2004 | Miller et al. |
| 6,865,416 B2 | 3/2005 | Dev et al. |
| 6,881,213 B2 * | 4/2005 | Ryan et al. ............. 606/41 |
| 6,892,099 B2 | 5/2005 | Jaafar et al. |
| 6,912,417 B1 | 6/2005 | Bernard et al. |
| 6,927,049 B2 | 8/2005 | Rubinsky et al. |
| 6,962,587 B2 | 11/2005 | Johnson et al. |
| 6,972,014 B2 | 12/2005 | Eum et al. |
| 6,994,706 B2 | 2/2006 | Chornenky et al. |
| 7,053,063 B2 | 5/2006 | Rubinsky et al. |
| 7,063,698 B2 | 6/2006 | Whayne et al. |
| 7,130,697 B2 | 10/2006 | Chornenky et al. |
| 7,211,083 B2 | 5/2007 | Chornenky et al. |
| 7,267,676 B2 | 9/2007 | Chornenky et al. |
| 7,387,626 B2 * | 6/2008 | Edwards et al. ............. 606/33 |
| 7,455,675 B2 | 11/2008 | Schur et al. ............. 606/139 |
| 7,771,401 B2 * | 8/2010 | Hekmat et al. ............. 604/246 |
| 8,511,317 B2 * | 8/2013 | Thapliyal et al. ............. 128/898 |
| 2001/0044596 A1 | 11/2001 | Jaafar |
| 2002/0010491 A1 | 1/2002 | Schoenbach |
| 2002/0055731 A1 | 5/2002 | Atala et al. |
| 2002/0077676 A1 | 6/2002 | Schroeppel et al. |
| 2002/0099323 A1 | 7/2002 | Dev et al. |
| 2002/0138117 A1 | 9/2002 | Son |
| 2002/0183735 A1 * | 12/2002 | Edwards et al. ............. 606/32 |
| 2002/0183740 A1 * | 12/2002 | Edwards et al. ............. 606/41 |
| 2002/0193831 A1 | 12/2002 | Smith, III |
| 2003/0009110 A1 | 1/2003 | Tu et al. |
| 2003/0060856 A1 | 3/2003 | Chornenky et al. |
| 2003/0088189 A1 | 5/2003 | Tu et al. |
| 2003/0130711 A1 | 7/2003 | Pearson et al. |
| 2003/0170898 A1 | 9/2003 | Gundersen et al. |
| 2003/0195406 A1 * | 10/2003 | Jenkins et al. ............. 600/374 |
| 2003/0208200 A1 | 11/2003 | Palanker et al. |
| 2003/0225360 A1 | 12/2003 | Eppstein et al. |
| 2004/0019371 A1 | 1/2004 | Jaafar et al. |
| 2004/0059328 A1 * | 3/2004 | Daniel et al. ............. 606/41 |
| 2004/0059389 A1 | 3/2004 | Chornenky et al. |
| 2004/0146877 A1 | 7/2004 | Diss et al. |
| 2004/0153057 A1 | 8/2004 | Davison |
| 2004/0199159 A1 * | 10/2004 | Lee et al. ............. 606/47 |
| 2004/0243107 A1 | 12/2004 | Mackoviak |
| 2004/0267189 A1 | 12/2004 | Mavor et al. |
| 2005/0043726 A1 | 2/2005 | McHale et al. |
| 2005/0049541 A1 | 3/2005 | Behar et al. |
| 2005/0165393 A1 | 7/2005 | Eppstein |
| 2005/0171523 A1 | 8/2005 | Rubinsky et al. |
| 2005/0171574 A1 | 8/2005 | Rubinsky et al. |
| 2005/0182462 A1 | 8/2005 | Chornenky et al. |
| 2005/0261672 A1 | 11/2005 | Deem et al. |
| 2005/0288730 A1 | 12/2005 | Deem et al. |
| 2006/0015147 A1 | 1/2006 | Persson et al. |
| 2006/0025760 A1 | 2/2006 | Podhajsky |
| 2006/0079883 A1 | 4/2006 | Elmouelhi et al. |
| 2006/0121610 A1 | 6/2006 | Rubinsky et al. |
| 2006/0212078 A1 | 9/2006 | Demarais et al. |
| 2006/0217703 A1 | 9/2006 | Chornenky et al. |
| 2006/0264752 A1 | 11/2006 | Rubinsky et al. |
| 2007/0016183 A1 * | 1/2007 | Lee et al. ............. 606/34 |
| 2007/0043345 A1 | 2/2007 | Davalos et al. |
| 2007/0118069 A1 | 5/2007 | Persson et al. |
| 2007/0203486 A1 * | 8/2007 | Young ............. 606/41 |
| 2008/0052786 A1 | 2/2008 | Lin et al. |
| 2008/0154259 A1 * | 6/2008 | Gough et al. ............. 606/41 |
| 2008/0167649 A1 * | 7/2008 | Edwards et al. ............. 606/41 |
| 2009/0062792 A1 | 3/2009 | Vakharia et al. |
| 2009/0228001 A1 * | 9/2009 | Pacey ............. 606/33 |
| 2009/0281477 A1 | 11/2009 | Mikus et al. |
| 2010/0049190 A1 | 2/2010 | Long et al. |
| 2010/0087813 A1 | 4/2010 | Long |
| 2010/0130975 A1 * | 5/2010 | Long ............. 606/41 |
| 2010/0222677 A1 * | 9/2010 | Placek et al. ............. 600/439 |
| 2011/0202053 A1 * | 8/2011 | Moss et al. ............. 606/41 |

(56) References Cited

U.S. PATENT DOCUMENTS

| | | | |
|---|---|---|---|
| 2012/0165813 A1* | 6/2012 | Lee et al. | 606/41 |
| 2012/0310236 A1* | 12/2012 | Placek et al. | 606/33 |
| 2013/0110106 A1* | 5/2013 | Richardson | 606/41 |

FOREIGN PATENT DOCUMENTS

| | | |
|---|---|---|
| WO | 0020554 | 4/2000 |
| WO | 0107583 | 2/2001 |
| WO | 0107584 | 2/2001 |
| WO | 0107585 | 2/2001 |
| WO | 2004037341 | 5/2004 |
| WO | WO2009137800 A2 | 11/2009 |

OTHER PUBLICATIONS

Andreason, Electroporation as a Technique for the Transfer of Macromolecules into Mammalian Cell Lines, *J. Tiss. Cult. Meth.*, 15:56-62, 1993.

Baker, et al., Calcium-Dependent Exocytosis in Bovine Adrenal Medullary Cells with Leaky Plasma Membranes, *Nature*, vol. 276, pp. 620-622, 1978.

Barber, Electrical Impedance Tomography Applied Potential Tomography, Advances in Biomedical Engineering, Beneken and Thevenin, eds., IOS Press, 1993.

Beebe, S.J., et al., Nanosecond pulsed electric field (nsPEF) effects on cells and tissues: apoptosis induction and tumor growth inhibition. PPPS-2001 Pulsed Power Plasma Science 2001, 28$^{th}$ IEEE International Conference on Plasma Science and 13$^{th}$ IEEE International Pulsed Power Conference, Digest of Technical Papers (Cat. No. 01CH37251). IEEE, Part vol. 1, 2001, pp. 211-215, vol. I, Piscataway, NJ, USA.

Blad, et al., Impedance Spectra of Tumour Tissue in Comparison with Normal Tissue; a Possible Clinical Application for Electrical Impedance Tomography, *Physiol. Meas.* 17 (1996) A105-A115.

Brown, S.G., Phototherapy of tumors. *World J. Surgery*, 1983. 7: p. 700-9.

BPH Management Strategies: Improving Patient Satisfaction, *Urology Times*, May 2001, vol. 29, Supplement 1.

Brown, et al., Blood Flow Imaging Using Electrical Impedance Tomography, *Clin. Phys. Physiol. Meas.*, 1992, vol. 13, Suppl. A, 175-179.

Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001.

Coates, C.W.,et al., "The Electrical Discharge of the Electric Eel, Electrophorous Electricus," Zoologica, 1937, 22(1), pp. 1-32.

Cook, et al., ACT3: A High-Speed, High-Precision Electrical Impedance Tomograph, *IEEE Transactions on Biomedical Engineering*, vol. 41, No. 8, Aug. 1994.

Cowley, Good News for Boomers, *Newsweek*, Dec. 30, 1996/Jan. 6, 1997.

Cox, et al., Surgical Treatment of Atrial Fibrillation: A Review, *Europace* (2004) 5, S20-S-29.

Crowley, Electrical Breakdown of Biomolecular Lipid Membranes as an Electromechanical Instability, *Biophysical Journal*, vol. 13, pp. 711-724, 1973.

Davalos, et al., Tissue Ablation with Irreversible Electroporation, *Annals of Biomedical Engineering*, vol. 33, No. 2, Feb. 2005.

Davalos, et al ., Theoretical Analysis of the Thermal Effects During In Vivo Tissue Electroporation, Bioelectrochemistry, vol. 61, pp. 99-107, 2003.

Davalos, et al., A Feasibility Study for Electrical Impedance Tomography as a Means to Monitor T issue Electroporation for Molecular Medicine, *IEEE Transactions on Biomedical Engineering*, vol. 49, No. 4, Apr. 2002.

Davalos, Real-Time Imaging for Molecular Medicine through Electrical Impedance Tomography of Electroporation, Dissertation for Ph.D. in Engineering-Mechanical Engineering, Graduate Division of University of California, Berkeley, 2002.

Dean, Nonviral Gene Transfer to Skeletal, Smooth, and Cardiac Muscle in Living Animals, *Am J. Physiol Cell Physiol* 289: 233-245, 2005.

Dev, et al., Sustained Local Delivery of Heparin to the Rabbit Arterial Wall with an Electroporation Catheter, *Catheterization and Cardiovascular Diagnosis*, Nov. 1998, vol. 45, No. 3, pp. 337-343.

Dev, et al., Medical Applications of Electroporation, *IEEE Transactions of Plasma Science*, vol. 28, No. 1, pp. 206-223, Feb. 2000.

Duraiswami, et al., Boundary Element Techniques for Efficient 2-D and 3-D Electrical Impedance Tomography, *Chemical Engineering Science*, vol. 52, No. 13, pp. 2185-2196, 1997.

Duraiswami, et al., Efficient 2D and 3D Electrical Impedance Tomography Using Dual Reciprocity Boundary Element Techniques, *Engineering Analysis with Boundary Elements* 22, (1998) 13-31.

Duraiswami, et al., Solution of Electrical Impedance Tomography Equations Using Boundary Element Methods, *Boundary Element Technology* XII, 1997, pp. 226-237.

Edd, J., et al., In-Vivo Results of a New Focal Tissue Ablation Technique: Irreversible Electroporaton, *IEEE Trans. Biomed. Eng.* 53 (2006) p. 1409-1415.

Erez, et al., Controlled Destruction and Temperature Distributions in Biological Tissues Subjected to Monoactive Electrocoagulation, *Transactions of the ASME: Journal of Mechanical Design*, vol. 102, Feb. 1980.

Fox, et al., Sampling Conductivity Images via MCMC, Mathematics Department, Auckland University, New Zealand, May 1997.

Gauger, et al., A Study of Dielectric Membrane Breakdown in the Fucus Egg, *J. Membrane Biol.*, vol. 48, No. 3, pp. 249-264, 1979.

Gehl, et al., In Vivo Electroporation of Skeletal Muscle: Threshold, Efficacy and Relation to Electric Field Distribution, *Biochimica et Biphysica Acta* 1428, 1999, pp. 233-240.

Gençer, et al., Electrical Impedance Tomography: Induced-Current Imaging Achieved with a Multiple Coil System, *IEEE Transactions on Biomedical Engineering*, vol. 43, No. 2, Feb. 1996.

Gilbert, et al., Novel Electrode Designs for Electrochemotherapy, *Biochimica et Biophysica Acta* 1334, 1997, pp. 9-14.

Gilbert, et al., The Use of Ultrasound Imaging for Monitoring Cryosurgery, Proceedings 6$^{th}$ Annual Conference, IEEE Engineering in Medicine and Biology, 107-111, 1984.

Glidewell, et al., The Use of Magnetic Resonance Imaging Data and the Inclusion of Anisotropic Regions in Electrical Impedance Tomography, *Biomed, Sci. Instrum.* 1993; 29: 251-7.

Gothelf, et al., Electrochemotherapy: Results of Cancer Treatment Using Enhanced Delivery of Bleomycin by Electroporation, *Cancer Treatment Reviews* 2003: 29: 371-387.

Griffiths, et al., A Dual-Frequency Electrical Impedance Tomography System, *Phys. Med. Biol.*, 1989, vol. 34, No. 10, pp. 1465-1476.

Griffiths, The Importance of Phase Measurement in Electrical Impedance Tomography, *Phys. Med. Biol.*, 1987, vol. 32, No. 11, pp. 1435-1444.

Griffiths, Tissue Spectroscopy with Electrical Impedance Tomography: Computer Simulations, *IEEE Transactions on Biomedical Engineering*, vol. 42, No. 9, Sep. 1995.

Gumerov, et al., The Dipole Approximation Method and Its Coupling with the Regular Boundary Element Method for Efficient Electrical Impedance Tomography, *Boundary Element Technology* XIII, 1999.

Hapala, Breaking the Barrier: Methods for Reversible Permeabilization of Cellular Membranes, *Critical Reviews in Biotechnology*, 17(2): 105-122, 1997.

Heller, et al., Clinical Applications of Electrochemotherapy, *Advanced Drug Delivery Reviews*, vol. 35, pp. 119-129, 1999.

Ho, et al., Electroporation of Cell Membranes: A Review, *Critical Reviews in Biotechnology*, 16(4): 349-362, 1996.

Holder, et al., Assessment and Calibration of a Low-Frequency System for Electrical Impedance Tomography (EIT), Optimized for Use in Imaging Brain Function in Ambulant Human Subjects, *Annals of the New York Academy of Science*, vol. 873, Issue 1, Electrical BI, pp. 512-519, 1999.

Huang, et al., Micro-Electroporation: Improving the Efficiency and Understanding of Electrical Permeabilization of Cells, Biomedical Microdevices, vol. 2, pp. 145-150, 1999.

(56) References Cited

OTHER PUBLICATIONS

Hughes, et al., An Analysis of Studies Comparing Electrical Impedance Tomography with X-Ray Videofluoroscopy in the Assessment of Swallowing, *Physiol. Meas.* 15, 1994, pp. A199-A209.

Issa, et al., The TUNA Procedure for BPH: Review of the Technology: The TUNA Procedure for BPH: Basic Procedure and Clinical Results, Reprinted from *Infections in Urology*, Jul./Aug. 1998 and Sep./Oct. 1998.

Ivanuša, et al., MRI Macromolecular Contrast Agents as Indicators of Changed Tumor Blood Flow, *Radiol. Oncol.* 2001; 35(2): 139-47.

Jaroszeski, et al., In Vivo Gene Delivery by Electroporation, *Advanced Drug Delivery Review*, vol. 35, pp. 131-137, 1999.

Kinosita, et al., Hemolysis of Human Erythrocytes by a Transient Electric Field, *Proc. Natl. Acad. Sci. USA*, vol. 74, No. 5, pp. 1923-1927, 1977.

Liu, et al., Measurement of Pharyngeal Transit Time by Electrical Impedance Tomography, *Clin. Phys. Physiol. Meas.*, 1992, vol. 13, Suppl. A, pp. 197-200.

Lundqvist, et al., Altering the Biochemical State of Individual Cultured Cells and Organelles with Ultramicroelectrodes, *Proc. Natl. Acad. Sci. USA*, vol. 95, pp. 10356-10360, Sep. 1998.

Lurquin, Gene Transfer by Electroporation, *Molecular Biotechnology*, vol. 7, 1997.

Lynn, et al., A New Method for the Generation and Use of Focused Ultrasound in Experimental Biology, *The Journal of General Physiology*, vol. 26, 179-193, 1942.

Miklavčič, et al., A Validated Model of an in Vivo Electric Field Distribution in Tissues for Electrochemotherapy and for DNA Electrotransfer for Gene Therapy, *Biochimica et Biophysica Acta* 1523 (2000), pp. 73-83.

Miklavčič, et al., The Importance of Electric Field Distribution for Effective in Vivo Electroporation of Tissues, *Biophysical Journal*, vol. 74, May 1998, pp. 2152-2158.

Miller, L., et al., Cancer cells ablation with irreversible electroporation, *Technology in Cancer Research and Treatment* 4 (2005) 699-706.

Mir, Therapeutic Perspectives of In Vivo Cell Electropermeabilization, *Bioelectrochemistry*, vol. 53, pp. 1-10, 2000.

Mir, L.M., et al., Electric Pulse-Mediated Gene Delivery to Various Animal Tissues, in Advances in Genetics, Academic Press, 2005, p. 83-114.

Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.

Mir, et al., Effective Treatment of Cutaneous and Subcutaneous Malignant Tumours by Electrochemotherapy, British Journal of Cancer, vol. 77, No. 12, pp. 2336-2342, 1998.

Mir, et al., Electrochemotherapy Potentiation of Antitumour Effect of Bleomycin by Local Electric Pulses, *European Journal of Cancer*, vol. 27, No. 1, pp. 68-72, 1991.

Mir, et al., Electrochemotherapy, a Novel Antitumor Treatment: First Clinical Trial, *C.R. Acad. Sci. Paris*, Ser. III, vol. 313, pp. 613-618, 1991.

Narayan, et al., Establishment and Characterization of a Human Primary Prostatic Adenocarcinoma Cell Line (ND-1), *The Journal of Urology*, vol. 148, 1600-1604, Nov. 1992.

Naslund, Michael J., Transurethral Needle Ablation of the Prostate, *Urology*, vol. 50, No. 2, Aug. 1997.

Naslund, Cost-Effectiveness of Minimally Invasive Treatments and Transurethral Resection (TURP) in Benign Prostatic Hyperplasia (BPH), (Abstract), Presented at 2001 AUA National Meeting Anaheim, CA, Jun. 5, 2001.

Neumann, et al., Gene Transfer into Mouse Lyoma Cells by Electroporation in High Electric Fields, *J. Embo.*, vol. 1, No. 7, pp. 841-845, 1982.

Neumann, et al., Permeability Changes Induced by Electric Impulses in Vesicular Membranes, *J. Membrane Biol.*, vol. 10, pp. 279-290, 1972.

Okino, et al., Effects of High-Voltage Electrical Impulse and an Anticancer Drug on In Vivo Growing Tumors, *Japanese Journal of Cancer Research*, vol. 78, pp. 1319-1321, 1987.

Onik, et al., Sonographic Monitoring of Hepatic Cryosurgery in an Experimental Animal Model, *AJR American J. of Roentgenology*, vol. 144, pp. 1043-1047, May 1985.

Onik, et al., Ultrasonic Characteristics of Frozen Liver, *Cryobiology*, vol. 21, pp. 321-328, 1984.

Organ, L.W., Electrophysiological principles of radiofrequency lesion making, *Apply. Neurophysiol.*, 1976. 39: p. 69-76.

Piñero, et al., Apoptotic and Necrotic Cell Death Are Both Induced by Electroporation in HL60 Human Promyeloid Leukaemia Cells, *Apoptosis*, vol. 2, No. 3, 330-336, Aug. 1997.

Rols, M.P., et al., Highly Efficient Transfection of Mammalian Cells by Electric Field Pulses: Application to Large Volumes of Cell Culture by Using a Flow System, *Eur. J. Biochem.* 1992, 206, pp. 115-121.

Rubinsky, B., ed, Cryosurgery. *Annu Rev. Biomed.* Eng. vol. 2 2000. 157-187.

Schmukler, Impedance Spectroscopy of Biological Cells, downloaded from IEEE Xplore website.

Sersa, et al., Reduced Blood Flow and Oxygenation in SA-1 Tumours after Electrochemotherapy with Cisplatin, *British Journal of Cancer*, 87, 1047-1054, 2002.

Sersa, et al., Tumour Blood Flow Modifying Effects of Electrochemotherapy: a Potential Vascular Targeted Mechanism, *Radiol. Oncol.*, 37(1): 43-8, 2003.

Sharma, et al., Poloxamer 188 Decreases Susceptibility of Artificial Lipid Membranes to Electroporation, *Biophysical Journal*, vol. 71, No. 6, pp. 3229-3241, Dec. 1996.

Shiina, S., et al, Percutaneous ethanol injection therapy for hepatocellular carcinoma: results in 146 patients. *AJR*, 1993, 160: p. 1023-8.

Thompson, et al., To determine whether the temperature of 2% lignocaine gel affects the initial discomfort which may be associated with its instillation into the male urethra, *BJU International* (1999), 84, 1035-1037.

Weaver, Electroporation: A General Phenomenon for Manipulating Cells and Tissues, *Journal of Cellular Biochemistry*, 51: 426-435, 1993.

Weaver, et al., Theory of Electroporation: A Review, *Bioelectrochemistry and Bioenergetics*, vol. 41, pp. 136-160, 1996.

Zimmermann, et al., Dielectric Breakdown of Cell Membranes, *Biophysical Journal*, vol. 14, No. 11, pp. 881-899, 1974.

Zlotta, et al., Possible Mechanisms of Action of Transurethral Needle Ablation of the Prostate on Benign Prostatic Hyperplasia Symptoms: a Neurohistochemical Study, Reprinted from *Journal of Urology*, vol. 157, No. 3, Mar. 1997, pp. 894-899.

Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001.

\* cited by examiner

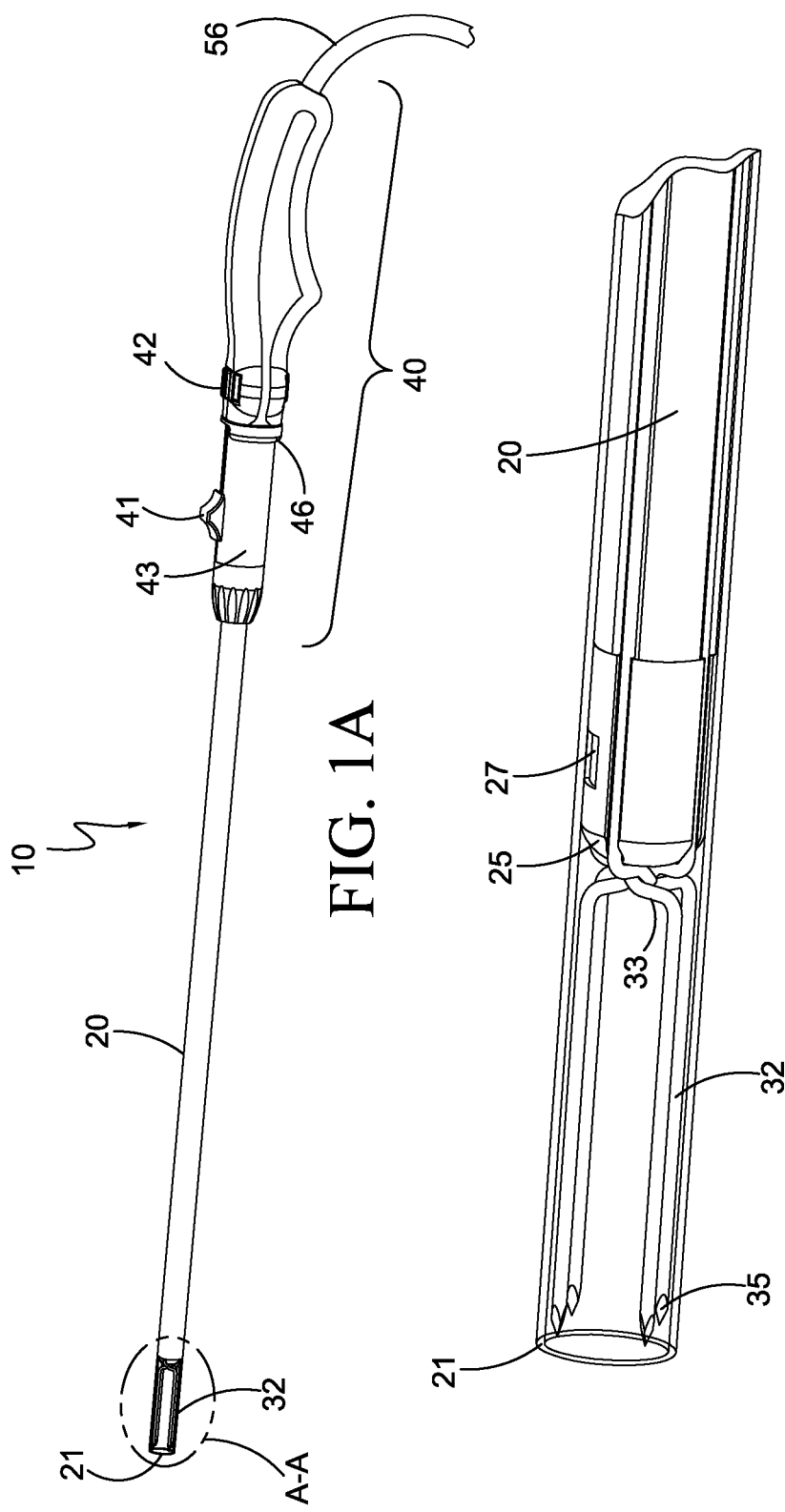

Section B-B

Section C-C

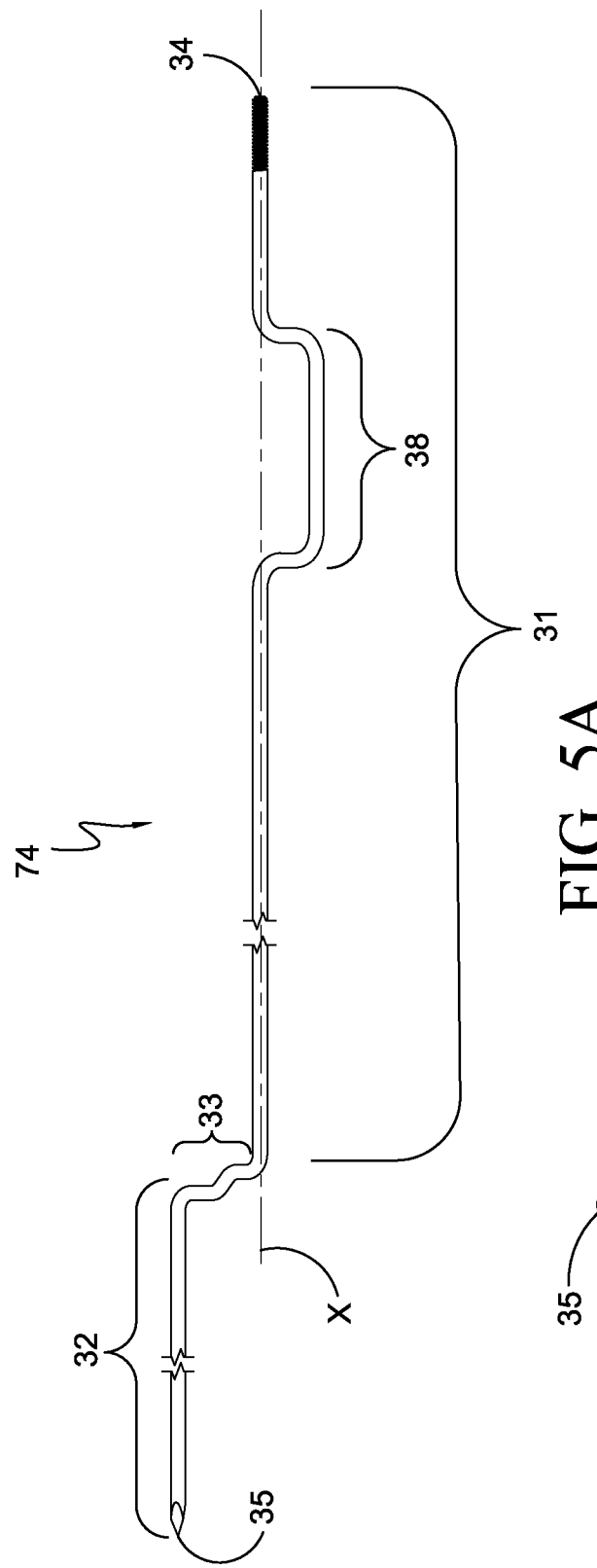
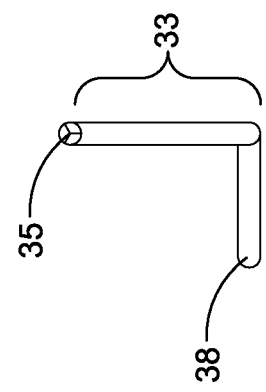
FIG. 5A
FIG. 5B

For Treating Tissue using the Therapeutic Energy Delivery Device

THERAPEUTIC ENERGY DELIVERY DEVICE WITH ROTATIONAL MECHANISM

CROSS REFERENCE TO RELATED APPLICATIONS

This application claims priority to U.S. Provisional Application Ser. No. 61/146,984, filed Jan. 23, 2009, which is incorporated herein by reference.

FIELD OF THE INVENTION

The present invention relates to a medical device and method for the ablation of diseased tissue. More particularly, the present application relates to a device for delivering therapeutic energy to tissue, and methods for using the same.

BACKGROUND OF THE INVENTION

Conventional devices for delivering therapeutic energy to tissue include a handle and a probe coupled to the handle. The probe contains at least one electrode to which an electrical power source is coupled. The power source allows the electrode to deliver the therapeutic energy to a targeted tissue, thereby causing ablation of the tissue.

In certain applications, it is desirable to provide a probe having a relatively small cross-section, for example 1 cm in diameter or less, wherein the electrodes are moved to a compact state to a configuration where the distance between the distal section of any two electrodes is smallest, so as to be placeable within a position inside of the outermost dimension of the probe. Prior art devices have utilized flexible materials having shape memory (such as nickel titanium, also known as "Nitinol") for the electrodes in order to accomplish this. However as the distal sections of the electrodes are moved from a compact position to a more expanded position where the distance between at least distal sections of two electrodes becomes greater, it is difficult to keep such electrodes in proper alignment if they are composed of flexible materials. Further, it is often difficult or sometimes not possible to place the electrodes in the correct location of the tissue to be ablated.

Applications of a probe that could be utilized as described ideally would involve the emerging technology of Irreversible Electroporation (IRE). Irreversible electroporation (IRE) involves the use of electrical pulses to target tumor tissue in the range of microseconds to milliseconds that can lead to non-thermally produced defects in the cell membrane that are nanoscale in size. These defects can lead to a disruption of homeostasis of the cell membrane, thereby causing irreversible cell membrane permeabilization which induces cell necrosis, without raising the temperature of the tumor ablation zone. During IRE ablation, connective tissue and scaffolding structures are spared, thus allowing the surrounding bile ducts, blood vessels, and connective tissue to remain intact. With nonthermal IRE (hereinafter also called non-thermal IRE), cell death is mediated through a nonthermal mechanism, so the heat sink problem associated with many ablation techniques is nullified. Therefore the advantages of IRE to allow focused treatment with tissue sparing and without thermal effects can be used effectively in conjunction with thermal treatment such as RF that has been proven effective to prevent track seeding; this will also allow (in this example embodiment) the user to utilize determined RF levels (or long-DC pulses) leading to in some cases ablation and in some cases coagulation of blood vessels of all sizes encountered during treatment. IRE can be utilized effectively with known techniques of thermal damage including mediating tumor cell death and bringing about coagulation along a tissue track.

Therefore, it would be desirable to provide a device and method which includes electrodes that can be placed within a relatively small diameter by being placed in a compact position to a more expanded position where the distance between at least distal sections of two electrodes becomes greater, and then returned to the compact position while the distal sections of the electrodes remain in parallel with each other. With some therapies, parallel electrodes are needed; parallel embodiments are in certain cases better than curved flexible electrodes such as in use with hard surfaces, tumors, or cancers. Maintaining a parallel orientation can be critical to treatment success. Additionally, this device could be used to mediate irreversible electroporation separately or in conjunction with reversible electroporation, long-DC pulses, and Radio-Frequency (RF) technologies which provides additional advantages of treatment when used in conjunction with features such as the parallel electrode orientation.

SUMMARY

Throughout the present teachings, any and all of the one, two, or more features and/or components disclosed or suggested herein, explicitly or implicitly, may be practiced and/or implemented in any combinations of two, three, or more thereof, whenever and wherever appropriate as understood by one of ordinary skill in the art. The various features and/or components disclosed herein are all illustrative for the underlying concepts, and thus are non-limiting to their actual descriptions. Any means for achieving substantially the same functions are considered as foreseeable alternatives and equivalents, and are thus fully described in writing and fully enabled. The various examples, illustrations, and embodiments described herein are by no means, in any degree or extent, limiting the broadest scopes of the claimed inventions presented herein or in any future applications claiming priority to the instant application.

Disclosed herein are devices for delivering therapeutic energy for destruction and/or removal of undesirable living biological tissues and methods of using such, particularly for treatment. In particular, according to the principles of the present invention, a device for delivering therapeutic energy to tissue is provided. The device includes a housing and a rotating device coupled to the housing. The device includes a plurality of electrodes, each electrode including: (i) a proximal section longitudinally extending from the within the housing and having a longitudinal axis; (ii) an intermediate section extending from the proximal section; and (iii) a distal section extending longitudinally from the intermediate section. The rotating device is coupled to the proximal sections of the plurality of electrodes and adapted to rotate the electrodes to move the distal section of the electrodes so that distance between at least two electrodes changes, so that the electrodes can be placed in a compact position or an expanded position or can be placed at any configuration, referring to any radial state between fully compacted and fully expanded.

BRIEF DESCRIPTION OF THE SEVERAL VIEWS OF THE DRAWINGS

FIG. 1A is an isometric view of a therapeutic energy delivery device of the present invention shown with the electrodes moved to a configuration where the distance between the distal section of any two electrodes is smallest and wherein the distal section of the electrodes are covered with the sleeve.

FIG. 1B is an enlarged partial isometric view of the distal portion of the therapeutic energy delivery device of FIG. 1A designated as Section A-A.

FIG. 5A-5B show a single electrode of the present invention where FIG. 5A is a plan view of an electrode of the therapeutic energy delivery device of FIG. 1-3A and FIG. 5B is a distal end view.

FIG. 13A shows the electrodes in configuration where the distance between the distal section of any two electrodes is smallest and FIG. 13B shows the electrodes in a configuration where the distance between the distal section of any two electrodes is greatest.

DETAILED DESCRIPTION

Figure 2A:
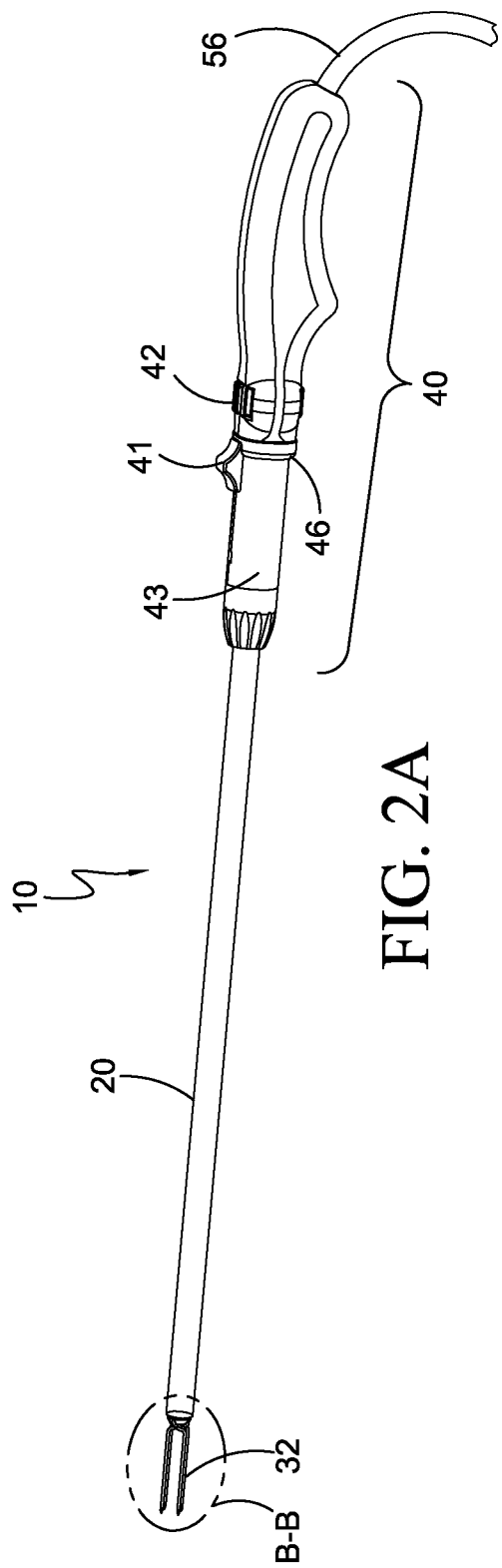
FIG. 2A is an isometric view of the therapeutic energy delivery device of the present invention shown with the electrodes in a configuration where the distance between the distal section of any two electrodes is smallest and wherein the sleeve has been moved to a position to uncover the distal sections of the electrodes.

"Therapeutic energy" and "TE", used interchangeably herein and in the contexts of "therapeutic energy delivery" and "TED", refer to the energy output from the treatment member(s) of the devices or portions thereof (e.g., distal segment(s) of the treatment member(s)) to its immediate surroundings, such as the target tissue(s) when present. Non-limiting examples of therapeutic energy include electromagnetic energy such as radio frequency energy, radiant thermal energy, radiation energy, acoustic energy (e.g., ultrasonic energy), and high voltage DC current creating electrical pulses. Also, the treatment can include therapies for irreversible electroporation as well as reversible electroporation (separately or in combination and with any of the previous energies or therapies indicated).

"Operator" refers to a person or a robotic assembly who uses the devices for treatments, particularly in patients (e.g., coagulation, ablation). The operator may be a physician, including interventional radiologists, oncologists, and surgeons.

The term "distal" is understood to mean away from a medical practitioner and towards the body site at which the procedure is performed, and "proximal" means towards the medical practitioner and away from the body site.

The present invention is illustrated in FIGS. 1 through 17. FIG. 1A is an isometric view of a therapeutic energy delivery device 10 of the present invention with the electrodes 74 protected by a sleeve 21 for an embodiment having four individual electrodes. Shown in FIG. 1A is the therapeutic energy delivery device 10, having a housing 40 (also called a hand piece) as well as a stabilizer 20 (also called an elongated shaft). A coupling 56 for the therapeutic energy delivery device provides coupling with a power source or energy source (not shown). Also shown in FIG. 1A is the distal section 32 of the electrodes of the therapeutic energy delivery device 10 as well as a sleeve 21 covering the distal section 32 of the electrodes. Shown attached to the housing 40 is a rotational cam 42 (also called a rotating collar) that functions to rotate the electrodes such that the overall diameter of the electrode group can be increased or decreased. When rotated to a compact configuration, the distal sections of 32 of the electrode group have the advantage of insertion of the electrodes into a small diameter opening electrodes move into an expanded radial state where the distance between the distal section of any two electrodes becomes greater, allowing for a larger treatment area than the size of the opening. In one embodiment, the elongated shaft 20 has a diameter of about 1 cm or less. The elongated shaft 20 is capable of being inserted into a lumen of a laparoscopic trocar (not shown) during use. Also shown in FIG. 1 is a slide 41 that allows for the sleeve to be moved distally or proximally to respectively cover or uncover the electrodes. Collar 46 is a structural component that the retractor 43 rests against in embodiments where the retractor 43 is immobilized, and a component that the retractor 43 abuts in embodiments where the retractor 43 is moveable when retractor 43 is moved to a most proximal position. This provides stability for the subassembly of the device in rapid electrode state changes. Also, a plurality of tabs 27 lock the cap 25 position and prevent twisting of the cap 25 when the radial state is adjusted, altering the distance between distal sections 32 of the electrodes.

Still referring to FIG. 1A, the slide 41 can be coupled to an assembly or subassembly that may include a retractor 43 having sections known in the art to allow for the electrodes to be locked in place such that no rotation is possible when the sleeve 21 is moved to a distal position to cover the distal section of the electrodes. The slide can be located on the top, side, or bottom of the device and can be a trigger, knob, switch, or other mechanical or electrical device known in the art to provide for movement of the sleeve 21. In certain embodiments a knob coupled to the handle rotates and the sleeve can be moved proximally and distally.

FIG. 1B is an enlarged isometric view of the distal portion of the therapeutic energy delivery device of FIG. 1A designated as Section A-A. Shown is the stabilizer 20, the distal section 32 of the electrodes in a configuration where the distance between the distal section of any two electrodes is smallest, and wherein the distal sections 32 of the electrodes are covered by a sleeve 21 that has been moved distally to cover as well as to protect the distal sections of the electrodes. Also shown is an intermediate section 33. For completeness a tab 27 and cap 25 are shown. A plurality of tabs 27 lock the cap 25 position and prevent twisting of the cap 25 when the radial state is adjusted, altering the distance between distal sections 32 of the electrodes.

The therapeutic device has electrodes that extend through an elongated shaft and extend out of the distal end of the elongated shaft, The electrodes are capable of rotation from a controller such as a rotating device coupled to the handle of the therapeutic device such that the electrodes can be placed in multiple positions; the electrodes can be overlapped at the intermediate section to form a compact, minimum diameter position wherein the electrodes fit within the longitudinal cross-sectional perimeter of the elongated shaft, and the electrodes can also be rotated in the opposite direction so as to extend out to a point that reaches to or even beyond the perimeter of the cross-section of the longitudinal shaft. The electrodes can be positioned at any overlapping position between fully overlapped and fully extended and can be operable so as to deliver voltage for treatment at any position. In certain embodiments the rotation in either direction changes the diameter between the distal sections of at least two electrodes and in various embodiments there is no elongated shaft. In certain embodiments the position of the distal section of the electrodes is called a radial state and the device can be set to have any radial state between a minimum and maximum position and be capable of delivering voltage for treatment. For example, one radial state would be when the distal section of the electrodes are moved to a configuration where the distance between the distal section of any two electrodes is smallest, while another radial state would be a configuration where the distance between the distal section of any two electrodes was greatest. This would represent a compact shape and an expanded state respectively and at each radial state the distal sections of the electrodes would be capable of delivering voltage for treatment. Also, any radial state between those two configurations also would allow for the capability of treatment. In various embodiments of the present invention, the user has indicators that show the radial state, the potential ablation zone, the distance between any two electrodes, and any other factors significant for preparing for ablation. The indicators can be mechanical, electrical, or software-mediated indicators on the rotational cam 42 or the elongated shaft 20 so that the user knows at any given time the ablation to be carried out by used voltage. The indicators can also include the insulation position or amount of exposed or active electrodes. Also, software can keep track of and show through a 3D model or through numbers on a computer screen how compact or expanded the, radial state is for use (including the numbers described such as distance between electrodes). The ends of the electrodes can also have indicators that allow better actual visualization for any scans of the body.

The electrodes can in certain embodiments be covered by a sleeve that can be moved by a controller at the handle to either move the sheath to a position where the electrodes are covered or move the sleeve so the distal section of the electrodes are uncovered. When the electrodes are covered the electrodes are protected. When the electrodes are covered, in certain embodiments, the electrodes in various embodiments become locked in place and cannot be rotated.

In various embodiments the elongated shaft 20 includes a sleeve 21 that surrounds and protects the distal sections 32 of the electrodes while the device is being inserted into a body through the lumen of a laparoscopic trocar. A "body" can refer to a human or mammal or other non-mammal or organism requiring treatment. The sleeve 21 is in certain embodiments attached to a retractor 43 to form a subassembly. A slide 41 controls advancement of the sleeve and in certain embodiments controls the retraction of the retractor 43 (The retractor embodiment in FIG. 1 cannot move).

In various embodiments a rotating device or rotating collar 42 is coupled to the hand piece 40. The rotating collar 42 will be described in further detail in subsequent figures such as FIG. 4.

Referring to FIG. 1B, a plurality of electrodes extend within the elongated shaft 20. The number of electrodes can be one or more. The distal sections 32 of the electrodes and the proximal sections 31 of the electrodes (the proximal sections are not shown in FIG. 1B though this is clearly shown in FIG. 5) are in parallel with each other in all distal electrode configurations possible upon rotation. Preferably, the electrodes are rigid which helps to ensure that the orientation of the electrodes relative to each other is constant (for example, ensuring that the electrodes remain in a parallel configuration to each other). In one embodiment, the electrodes are approximately 0.040" in diameter and are made of stainless steel The sleeve 21, when advanced to its most distal position, has been extended out from the elongated shaft 20. In certain embodiments the shaft or portions of the shaft include in whole or in part sections made of biologically compatible materials (e.g., stainless steel, titanium, alloys thereof), and in certain embodiments is comprised of a solid core and in other embodiments has a plurality of channels for receiving the proximal sections 31 of the electrodes. The electrodes are isolated from the metal shaft through moveable or immoveable insulation that extends distally through the proximal sections 33 of the electrodes. A cap 25 is in certain embodiments positioned at the distal end of the elongated shaft 20, In certain embodiments a seal is optionally provided between the cap 25 and the stabilizer. The distal sections 32 of the electrodes extend out of the cap 25 for delivering the therapeutic energy to the tissue. A plurality of tabs 27 can lock the cap 25 position and prevent twisting of the cap 25 during use of the device. The tips 35 of the electrodes can be sharp for piercing tissue.

Each electrode can be insulated (insulation layer not shown). The insulation preferably runs up to about 2.5 cm from the distal tip 35. although the electrodes may have an exposable longitudinal length of 0.5 cm or greater and/or 10 cm or less, such as 1 cm, 2 cm, 2.5 cm, 3 cm, 4 cm, 5 cm, 6 cm, 8 cm, or a range between any two of such values. The uninsulated or exposed electrode length defines the treatment section of the electrodes. It is preferred that the insulation layer covers the electrodes at any location where overlap with another electrode is possible, such as along the intermediate sections 33 of the electrodes. The insulation layer can run along the entire length of the proximal section of each electrode. The insulation layer can be variable or it can be fixed. If the insulation layer is fixed, it at least covers the intermediate section 33 of the electrode, but the insulation layer may also extend to surround a portion of the distal section 32 of the electrode. The insulation layer can be sprayed on, formed as shrink tubing, formed as a dipped material, or extruded as an outer layer. The electrodes can be non-insulated or insulated with a fixed or slidable insulation layer.

Figure 2B:
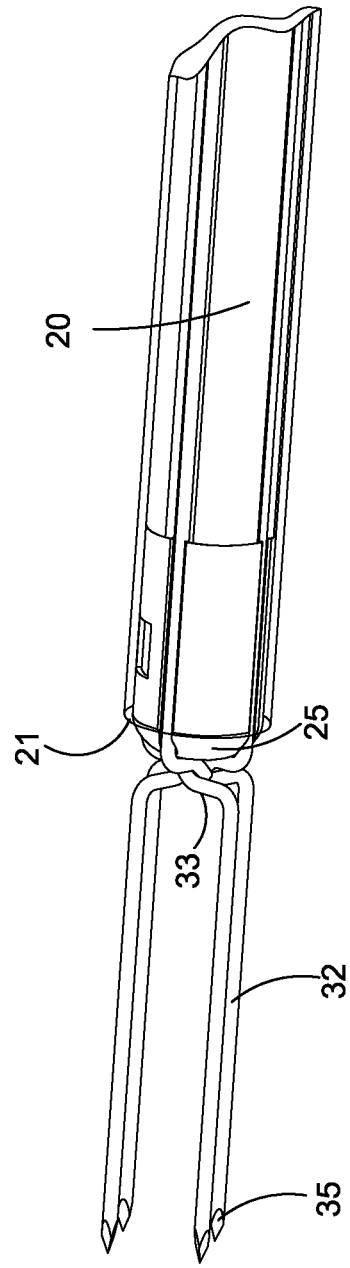
FIG. 2B is an enlarged partial isometric view of the therapeutic energy delivery device of FIG. 2A designated as Section B-B.

FIG. 2A is an isometric view of the therapeutic energy delivery device of the present invention being shown with the electrodes in a configuration where the distance between the distal section of any two electrodes is smallest. FIG. 2B is an enlarged isometric view of the therapeutic energy delivery device of FIG. 2A designated as Section B-B.

FIGS. 2A and 2B depict the same embodiment as FIGS. 1A-B, where the slide 41 has been moved proximally so as to pull back the sleeve 21 to a proximal position so that the distal sections 32 of the electrodes are uncovered. The sleeve 21 can be placed over the distal sections of the electrodes as in FIGS. 1A-B during insertion into a target region so as to protect the electrodes and to protect organs from inadvertent puncture by electrode tips, and the sleeve 21 can be moved proximally to expose the distal sections of the electrodes for treatment, as shown in FIGS. 2A-B. The treatment can be performed at any level or position of distal electrode configuration, referring to any radial state.

The distal sections 32 of the electrodes are fully exposed and are in a parallel arrangement with each other. The electrodes overlap each other at intermediate sections of the electrodes 33. The intermediate sections of the electrodes 33 can include a shape that allows for the overlap with multiple electrodes as shown in FIG. 2B and FIG. 5. For example, the intermediate sections of the electrodes 33 can include a bend or bends to allow the electrodes to overlap each other. Alternatively, the intermediate sections 33 of the electrodes do not include any bends, but instead the distal sections 32 of the electrodes have different lengths in order to accommodate the overlapping arrangement.

Figure 3A:
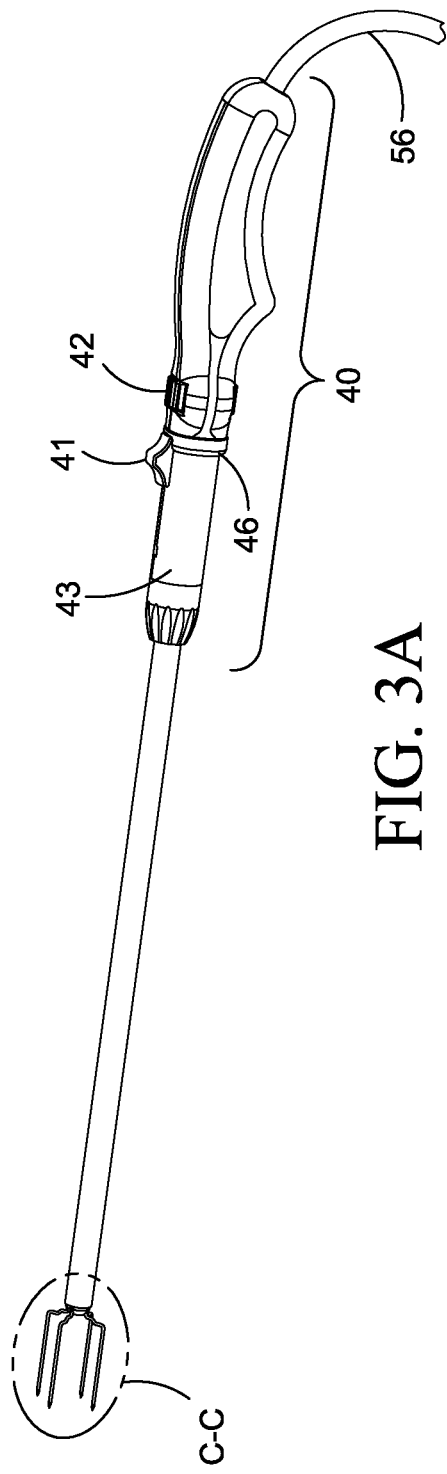
FIG. 3A is an isometric view of the therapeutic energy delivery device of the present invention shown with the electrodes in an expanded state where the distance between the distal section of any two electrodes is greatest, and with the sleeve in a position so as to uncover the distal section of the electrodes.

FIG. 3A is an isometric view of the therapeutic energy delivery device of the present invention shown with the electrodes in a maximum expanded state where the distance between the distal section of any two electrodes is greatest, and with the sleeve in a position so as to uncover the distal section of the electrodes.

Figure 3B:
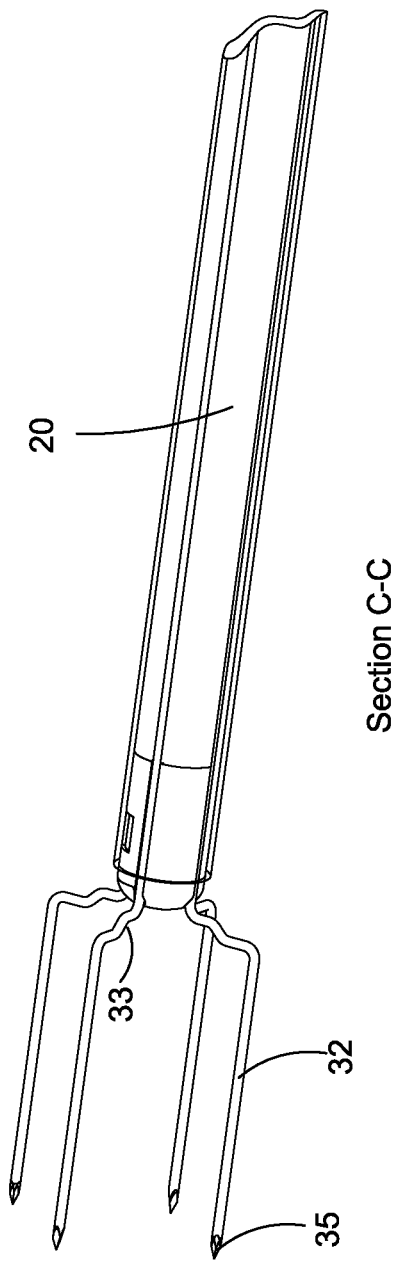
FIG. 3B is an enlarged partial isometric view of the therapeutic energy delivery device of FIG. 3A designated as Section C-C.

FIG. 3B is an enlarged isometric view of the therapeutic energy delivery device of FIG. 3A designated as Section C-C.

In certain embodiments the distance between any electrode is greater than the diameter of the stabilizer.

Referring to FIGS. 3A-3B, as the distal portions of the electrodes are moved to an expanded configuration from the compact configuration shown in FIGS. 2A-B, each of the electrodes undergoes identical angular rotation, such that all electrodes remain in a parallel configuration, spiraling in the form of an expanding cylinder. Preferably, the total amount of rotation that is possible is about 180 degrees from a compact configuration shown in FIGS. 2A-B to the expanded configuration that is the radial state shown in FIGS. 3A-B. It is preferred that the distal sections of the electrodes 32 remain in a parallel configuration through all possible configurations. This is particularly advantageous because it allows a predictable orientation of electrodes upon rotation. Further, it is important that the distal sections of the electrodes 32 remain in a parallel configuration when the therapeutic energy is delivered between the electrodes.

The distal sections 32 of the electrodes deliver therapeutic, energy to tissue. In one embodiment the distal sections 32 of the electrodes deliver electrical energy to achieve irreversible electroporation (IRE) energy in order to permanently open the cell membranes leading to tissue death, In another embodiment, radiofrequency energy can be applied to the electrodes. The energy source (not shown) is connected to the therapeutic device and delivers the energy to the electrodes. In one is connected to the therapeutic device and delivers the energy to the electrodes. In one embodiment, the electrodes are mono-polar electrodes and only two electrodes deliver energy at any given moment wherein one electrode is positive and one electrode is negative. The operator may program the energy source according to a predetermined energy delivery pattern as disclosed, for example, in U.S. Pat. No. 5,674,267 issued to Mir et al., which is incorporated herein by reference. As an example, if the device includes four electrodes (electrodes 1-4) as shown in FIG. 3B, and assuming that the electrodes are numbered 1 through 4 in a circumferential direction, the electrode firing sequence may be (1) electrode 1 (+)-electrode 2 (−); (2) electrode 2 (+)-electrode 3 (−); (3) electrode 3 (+)-electrode 4 (−); (4) electrode 4 (+)-electrode 1 (−); (5) electrode 1 (+)-electrode 3 (−); and (6) electrode 2 (+)-electrode 4 (−). In another embodiment, each electrode is a bipolar electrode. In one embodiment, both pairs of electrodes can fire simultaneously rather than sequential firing of individual pairs.

Figure 4:
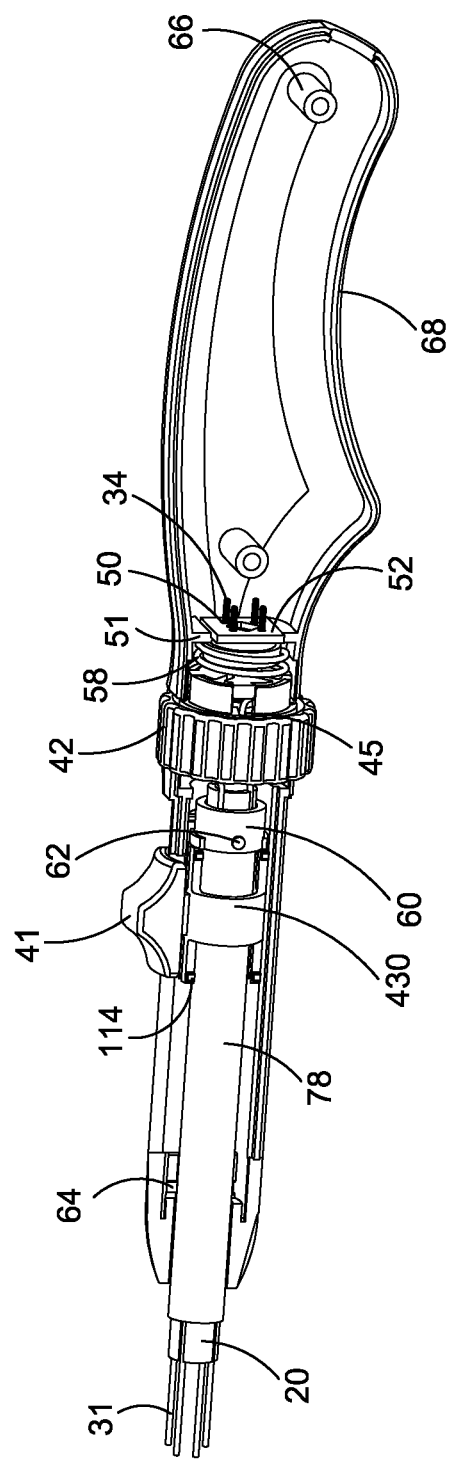
FIG. 4 is a partial cut-out perspective view of the hand piece of the therapeutic energy delivery device of FIG. 2A.

FIG. 4 is a partial cut-out perspective view of the hand piece of the therapeutic energy delivery device of FIG. 2A, and parts of FIG. 2A. Shown is the half-handle 68 of the hand piece, with a proximal handle protrusion 66 shown that can be used to hold, snap-fit, or be part of a mechanism to adhere or hold the handle parts or halves together. Also shown is the proximal end 34 of each electrode placed through supporting member 52 (also called bearing block). The support member 52 can lock into a support plate 51 that is attached to or is part of the housing to prevent unintentional movement of the distal sections 32 of the electrodes to a different radial state. In various embodiments the supporting member 52 interlocks with support plate 51 when the slide 41 is in its most distal position, when the sleeve is covering the distal section of the electrodes. Alternative embodiments allow locking in place when the sleeve is moved to a position where the distal section of the electrodes are uncovered. Also shown in FIG, 4 are: apertures 50 that are adapted to receive the proximal ends of each electrode 34, as well as the rotating collar 42 with slots 45 within the rotating collar (clearly depicted in FIGS. 6A-C), the stabilizer 20 that in this pictured embodiment is shown with a trocar 78 of the therapeutic energy device surrounding the stabilizer 20, and the proximal sections 31 of the electrodes just proximal to the intermediate sections of the electrodes (not shown). For completeness, the way the slide snaps in when it is in a distal position are now described since these parts are shown in FIG. 4. Slide 41 when moved distally can lock in place when snap-fit 114 mechanically slides into place into detent with pocket for snap-fit 64. When force is put on the slide to move it in a proximal direction, the slide moves proximally as snap-fit 114 slides out of pocket for snap-fit 64. In other words when the slide is moved distally it snaps in place and when moved proximally it mechanically slides out of snap-fit 64 and can be moved proximally.

Still referring to FIG. 4, FIG. 4 shows certain components housed partially or fully in the half-handle 68 of the hand piece 40 (not shown) of FIGS. 1A and 2A. Hand piece 40 may be composed of separately molded left and right pieces that are coupled together by adhesives or screws. A rotating collar 42 is coupled to the hand piece 40. The rotating collar 42 is positioned so that it can rotate about its axis which runs parallel to the elongated shaft 20. The rotating collar 42 in various embodiments includes a plurality of ridges along its outer surface for providing a gripping surface. At least a portion of the outer surface of the rotating collar 42 is exposed outside of the hand piece 40. The rotating collar 42 includes a plurality of slots 45 along its inner surface (more clearly depicted in FIGS. 6A-6C). Each proximal section of the electrode includes a "U-shaped" section 38 (depicted in FIG. 5) near the proximal end. The longitudinally extending bottom portion of each "U shaped" section 38 of each electrode runs through each corresponding slot 45. Though section 38 forms a "U shaped" section shown in FIG. 5, the shape can be defined as any shape known in the art so as to allow rotation of the electrodes when the rotating collar is moved. This could include electrodes with V-shapes or squares, or even single or multiple bends of zero to ninety degrees or more, or an electrode with undulations, among other configurations.

FIG. 4. also shows that the proximal ends 34 of the electrodes extend proximally through a supporting member 52 (also depicted in FIG. 9) within the handle that is for anchoring, supporting, and securing the position of the electrodes; this supporting member can be a single piece, molded or formed or created via any method known in the art. In FIG. 4 this supporting member is shown as two approximate rectangles and a rounded middle portion. In certain embodiments the supporting member comprises a pair of retaining plates that form a recess therebetween. The recess receives a support plate 51 (also depicted in FIG. 7) that extends from at least one side of the inner surface of the hand piece 40. The supporting member thereby is attached to the support plate 51 to form a secure fit in order to anchor the supporting member in a fixed position. The supporting member includes a plurality of apertures 50 that are adapted to receive the proximal ends of each electrode 34. As shown in FIG. 4, the apertures 50 of the supporting member thereby provide a fixed axis for the rotation of the proximal section of each electrode (the proximal ends of which, 34, can be seen clearly in the FIG. 4).

FIG. 5A-5B show a single electrode of the present invention where FIG. 5A is a plan view of an electrode of the therapeutic energy delivery device of FIG. 1-3A and FIG. 5B is a distal end view.

Still referring to FIGS. 5A-B, FIG. 5A-5B show a single electrode 74 of the present invention. 5B is a distal end view of the electrode and 5B is a side view rotated 45° from end view 5B to more clearly illustrate both offset sections 32 and 38. The electrode is comprised of a conductive material such as stainless steel, nitinol, or other metals or conductive plastics known in the art, and may have a uniform cross-sectional outer diameter of from 0.001" to 0.080" along its length. In one embodiment the overall length of electrode 74 is approximately 19 inches. The electrode includes: (i) a proximal section 31 longitudinally extending from the housing surface (not shown) and having a first longitudinal axis X; (ii) an intermediate section 33 extending from the proximal section 31 extending radially outward from the first longitudinal axis X; and (iii) a distal section 32 extending longitudinally from the intermediate section 33 on a second longitudinal axis parallel to axis X. The proximal section 31 extends from proximal electrode end 34 for approximately 17.5" to intermediate section 33. Although not shown, electrode end 34 is coupled to an electrical wire or other element which extends through coupling 56 of FIG. 1A for transmission of energy from the energy source to the electrode. Intermediate section 33 further includes a "U-shaped" section 38 having a longitudinal length of approximately 0.65 inches. Section 33 is outwardly off-set from longitudinal axis X by approximately 0.25" at a 90° angle relative to section 38, as shown in FIG. 5B. Intermediate section 33 is comprised of a stepped section consisting of two bends. The stepped profile of intermediate section 33 functions to provide a nested overlap of the electrodes when in a minimum diameter position, as will be described in more detail below. Distal section 32 of electrode 74 extends for approximately 1.3 inches from intermediate section 33 to sharpened distal tip 35. Distal section 32 is outwardly off-set from longitudinal axis X by approximately 0.32 inches. An insulative covering, not shown, is coaxially arranged around electrode 74 and extends from proximal end 34 to distal end section 32 where it terminates proximal to the distal end 35.

Figure 6A:
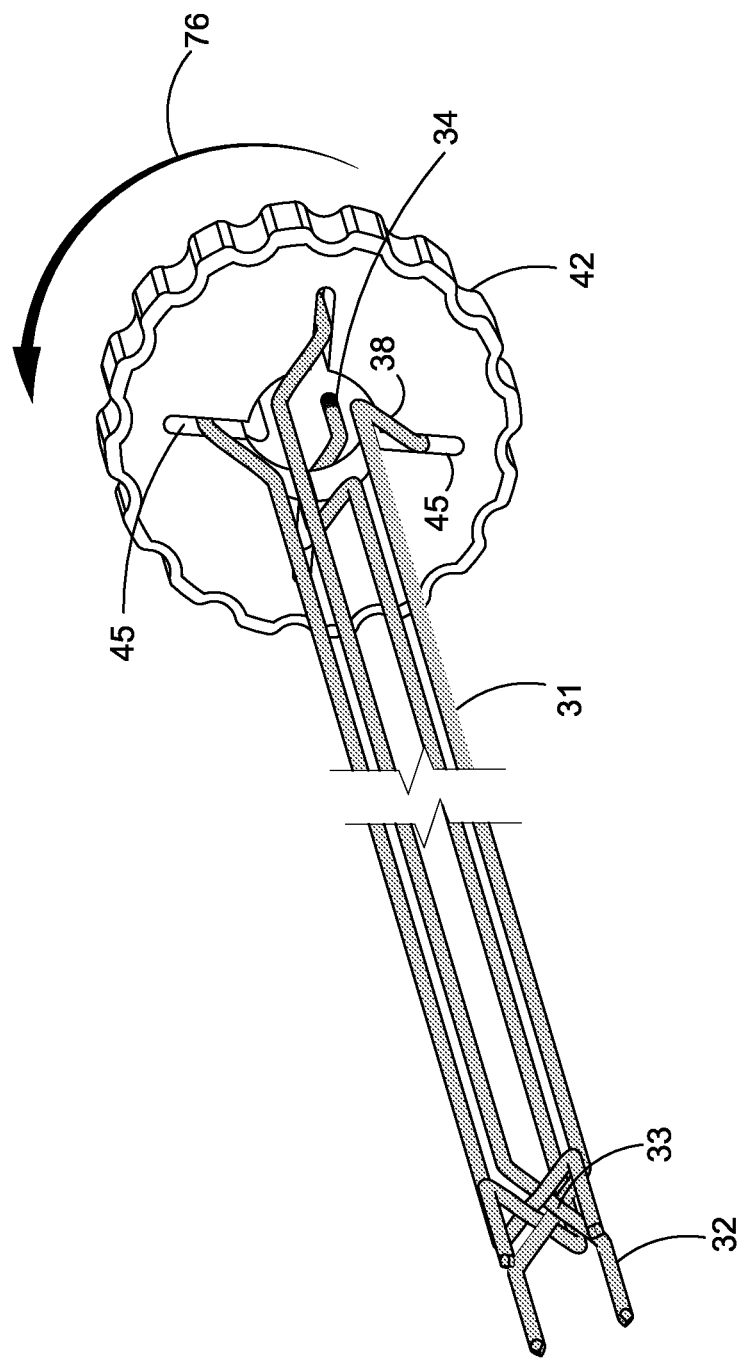
FIG. 6A is an enlarged isometric view of the electrodes and rotational cam showing the electrodes in a configuration where the distance between the distal section of any two electrodes is smallest.
Figure 6B:
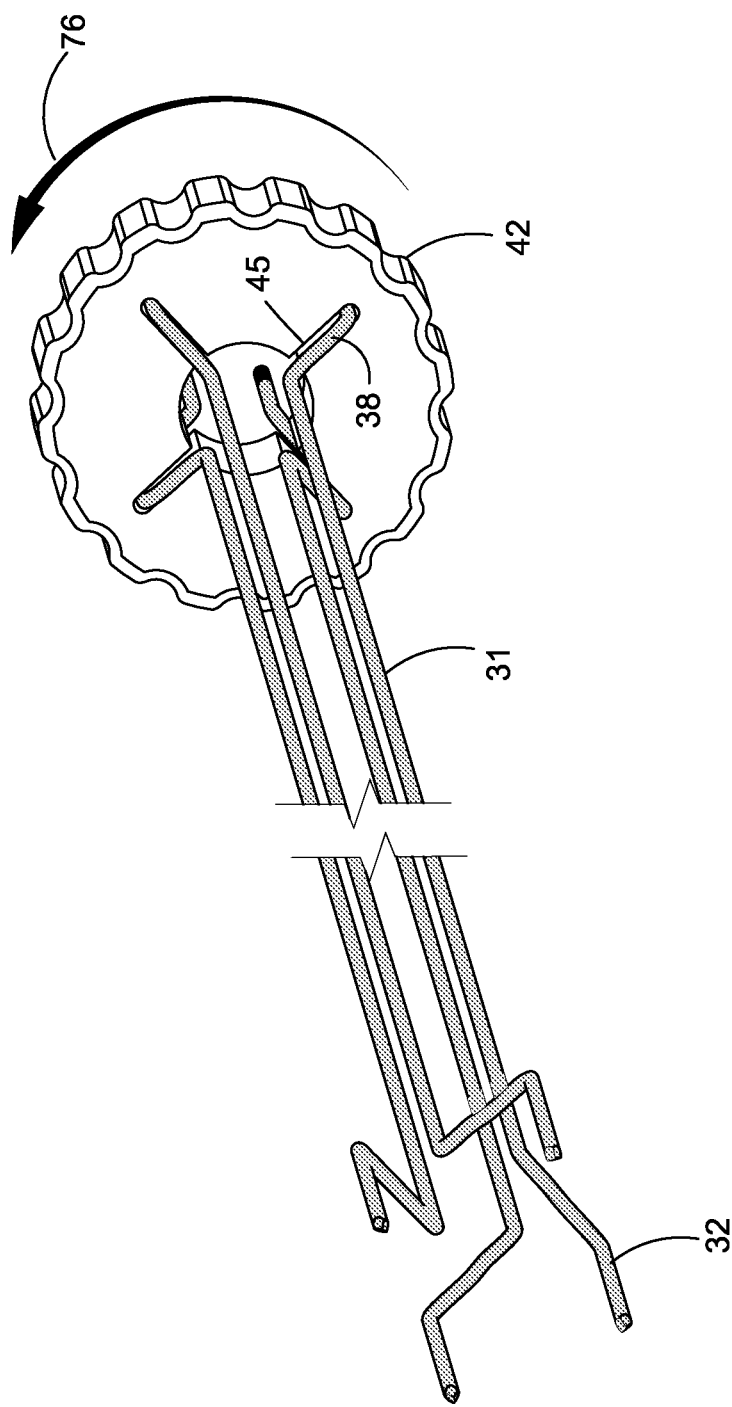
FIG. 6B is an enlarged isometric view of the electrodes and rotational cam subassembly showing the electrodes in a intermediate diameter configuration.
Figure 6C:
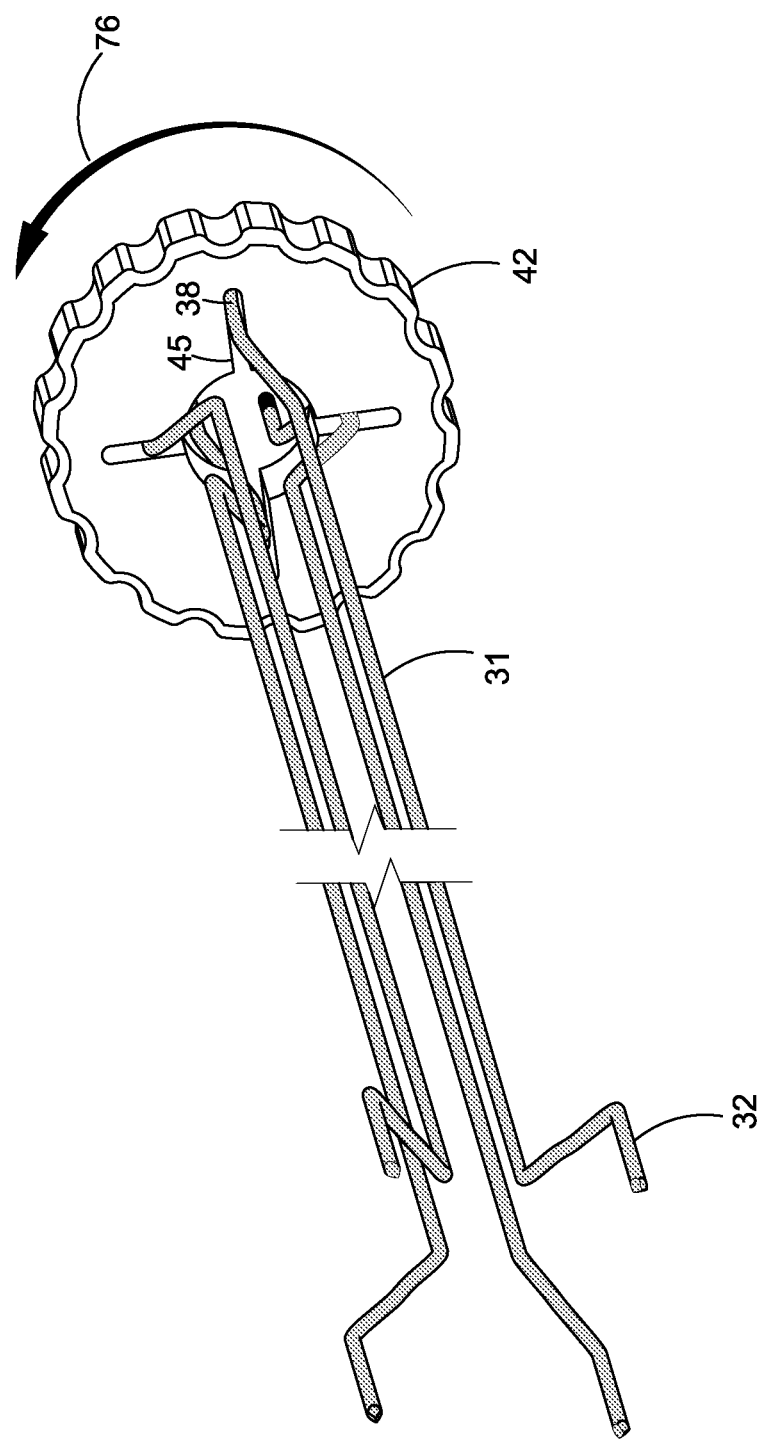
FIG. 6C is an enlarged isometric view of the electrodes and rotational cam subassembly showing the electrodes in a fully expanded position where the distance between the distal section of any two electrodes is greatest.

FIGS. 6A-6C show enlarged isometric views of the electrodes and rotational cam showing the electrodes first in a compact configuration where the distance between the distal section of any two electrodes is smallest (FIG. 6A), a second configuration in which the electrodes are at greater but not maximum distance relative to each other (FIG. 6B) and, a third configuration where the distance between the distal section of any two electrodes is greatest (FIG. 6C). FIGS. 6A-6C show the rotating collar 42, slots 45 within the rotating collar, as well as the "U-shaped" sections 38 of the electrodes, the proximal sections 31 of the electrodes, the intermediate sections 33 and the distal sections 32 of the electrodes. Arrow 76 shows the rotation direction as the rotating collar 42 is rotated from FIG. 6A to 6B to 6C respectively.

When the rotating collar 42 is rotated, the "U-shaped" sections 38 of the electrodes also move because they are captured within the slots 45. Therefore, as the rotating collar 42 is rotated the proximal section 31 of each electrode is caused to rotate about the longitudinal axis of the device thereby simultaneously causing the distal sections of the electrodes 32 to move radially outward as shown in FIG. 3A-B. Because the longitudinal axis of each proximal section 31 of each electrode is not centered within the rotating collar 42, the "U shaped" portion will slide radially within the slot 45 as the rotating collar 42 is rotated. Each slot 45 is properly sized so that the rotating collar 42 can rotate for a predetermined number of degrees (for example about 180 degrees) which in turn causes simultaneous rotation of the electrodes. For example, in certain embodiments when the electrodes are in a configuration where the distance between the distal section of any two electrodes is smallest (FIGS. 2A-B) the "U-shaped" section 38 is positioned near the innermost surface of the slot 45. As the rotating collar 42 is rotated about 90 degrees, the "U-shaped" section 38 moves radially to the outermost surface of the slot 45, as shown in FIG. 4. As the rotating collar 42 is continued to rotate for about another 90 degrees (for a total of about 180 degrees), the "U-shaped" section 38 moves radially back again near the innermost surface of the slot 45, at which point the electrodes are in a configuration where the distance between the distal section of any two electrodes is greatest (FIG. 3). In one embodiment, the slot 45 is sealed at both ends for preventing the "U-shaped" section 38 from inadvertently exiting the slot 45.

Figure 7:
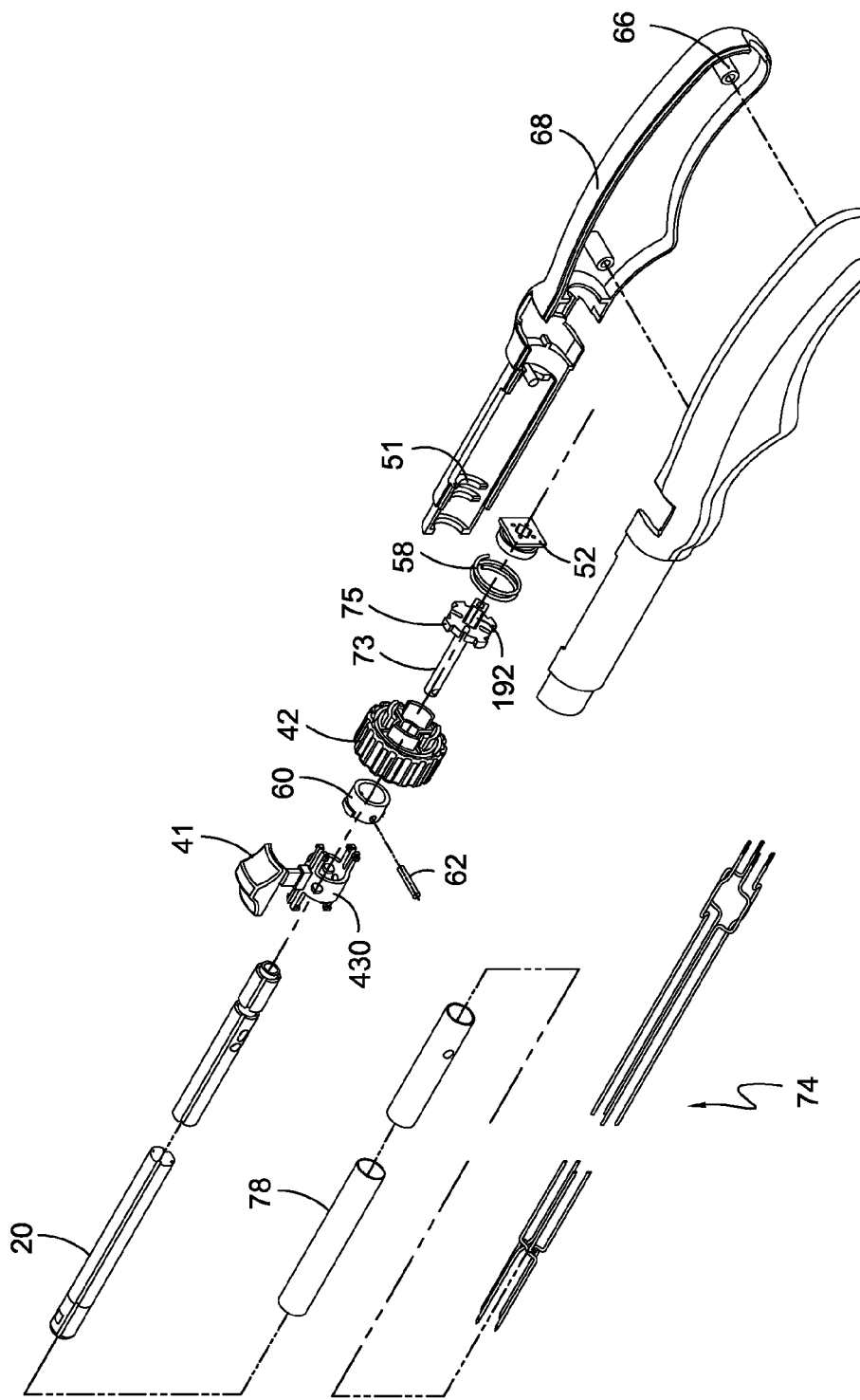
FIG. 7 is an exploded perspective view of the therapeutic energy delivery device of FIG. 1A illustrating the assembly components.

FIG. 7 is an exploded perspective view of the therapeutic energy delivery device of FIG. 1A. Shown are: the half-handle 68 of the hand piece with a proximal handle protrusion 66, the support plate 51 this supporting member 52, the spring 58, the lock shaft 72, the lock sleeve 60 with the lock pin 62, the alternative embodiment of the retractor 430, the slide 41, the stabilizer 20, the trocar 78, and the full electrodes 74. FIG. 7 is a holistic figure showing many parts of the device; there are four main sections shown, including the distal portions such as the electrodes 74 with the trocar 78 and stabilizer 20, the more proximal portions including those responsible for moving the sleeve forward and back via the slide 41 and retractor 430. Also shown are the parts responsible for rotation and locking of rotation when the slide is moved distally, such as the rotational cam 42 and the cam wheel lock element 75 of rotational lock component and the barrel portion 73 of the rotational lock component and the post section 192 of rotation lock component. Also shown are the handle portions that are most proximal and that provide stability.

Figure 8A:
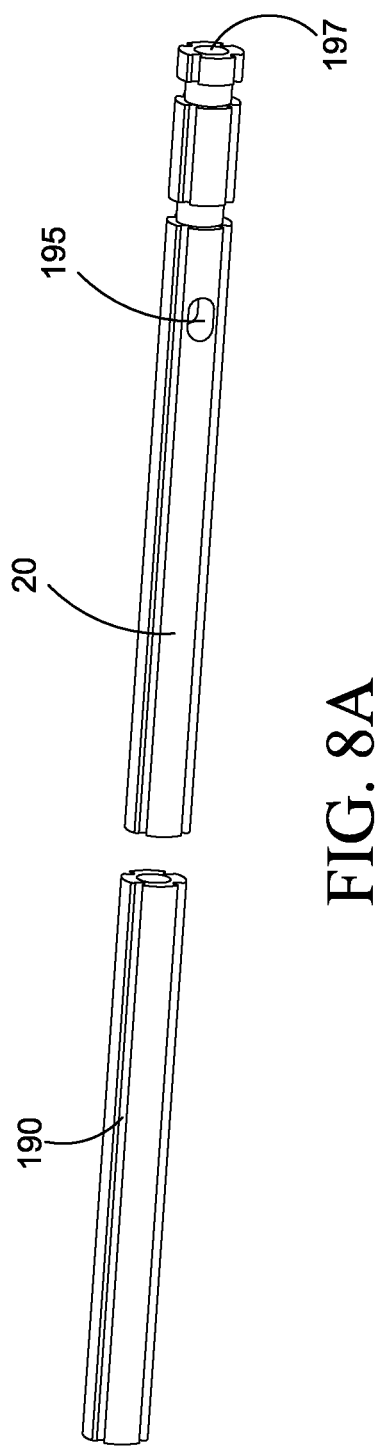
FIG. 8A is a plan view of the stabilizer component of the therapeutic energy delivery device of FIG. 1A.
Figure 8B:
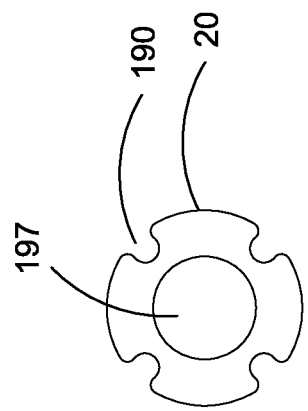
FIG. 8B shows a distal end view of the stabilizer.

FIG. 8A is a plan view of the stabilizer 20 component of the therapeutic energy delivery device of FIG. 1A, and FIG. 8B shows a distal end view of the stabilizer 20. In one embodiment, stabilizer 20 has an outer diameter of 0.34" with a central through channel 197 of approximately 0.185". Stabilizer 20 is preferably comprised of a medical grade stainless steel or other metal and includes a plurality of longitudinal electrode channels 190 in the outer surface of the stabilizer which extend the entire length of the stabilizer. Electrode channels 190 are approximately 0.050" in depth so as to accommodate the electrodes 74 completely within the channel 190. When the cam wheel 42 is rotated, electrodes 74 each rotate about their longitudinal axis (X in FIG. 5) within their respective channels 190. Stabilizer 20 with channels 190 function to ensure that during rotational movement of the electrodes around their X axis, the electrodes remain restricted within channels 190 preventing any horizontal or other movement.

Figure 9:
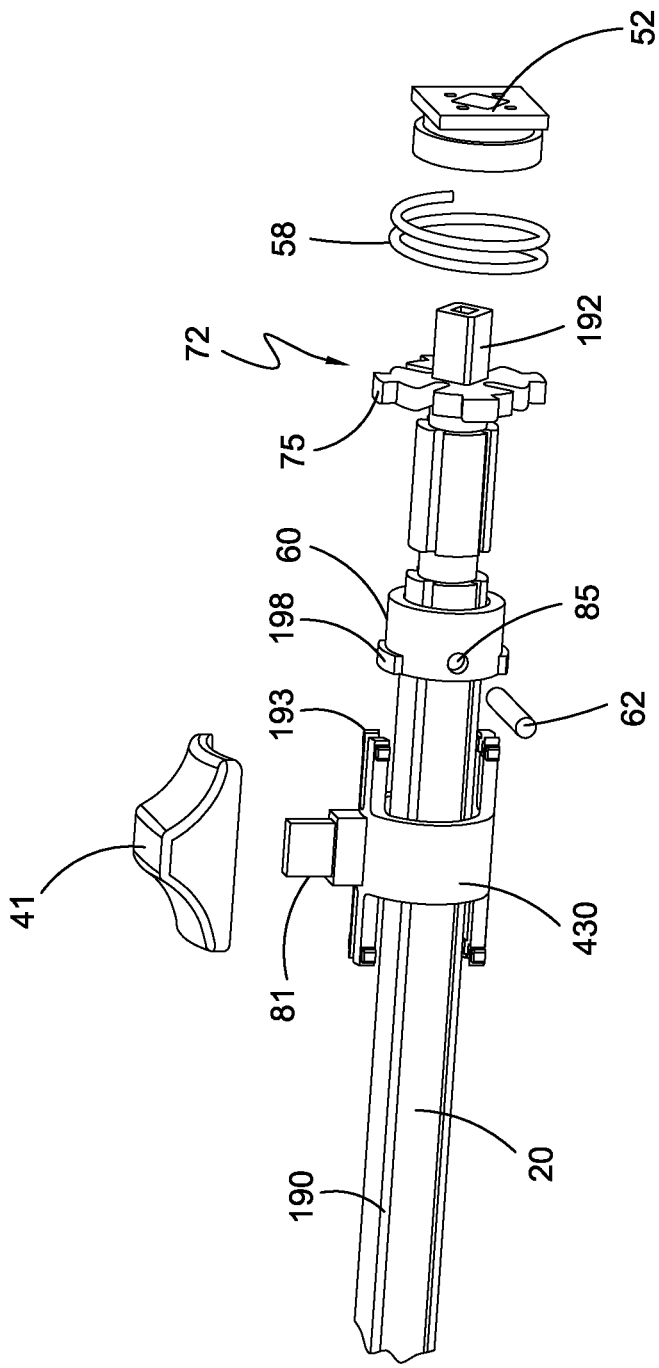
FIG. 9 is an exploded side view of the components of the slide mechanism of the therapeutic energy delivery device of FIG. 1A controlling the position of the sleeve.

FIG. 9 is an exploded isometric view of components of the slide mechanism that controls the movement of sleeve 21, as well as locking the cam 42 while in position so as to prevent any inadvertent radial expansion of the electrode group while covered by sleeve 21. The slide mechanism subassembly includes thumb slide 41 which is attached to retractor 430 by post 81 which fits into mating recess (not shown) in slide 41. Stabilizer 20 is coaxially arranged within the through lumen of retractor 430 allowing for longitudinal movement of the retractor when the thumb slide 41 is advanced or retracted. Trocar 78 (not shown), sleeve 21 and the plurality of electrodes 74 which are also positioned within the lumen of the retractor have been removed from FIG. 9 for clarity. Although not shown, sleeve 21 is fixably attached to retractor 430, so that longitudinal movement of thumb slide 41 causes a corresponding longitudinal movement of sleeve 21. Retractor 430 includes a plurality of longitudinally upper extending prongs of the retractor 193 which when slid proximally comes to abut up against lug 198 of lock sleeve 60, preventing any further longitudinal movement. Lock sleeve 60 is attached to stabilizer 20 by pin 62 which is received within hole 85 in the side wall of lock sleeve 60. Pin 62 is also aligned within through slot 195 (see FIG. 8A) of stabilizer 20 and pin 62 moves longitudinally within slot 195 of the stabilizer 20 in response to movement of the thumb slide. Longitudinal travel is limited to the length dimension of slot 195 which is approximately 0.1 inch in one embodiment (where the radius of either end is 0.05 inches). Also shown in FIG. 9 is rotational lock component 72 which includes a barrel portion 73, cam wheel lock element 75 and post section. When assembled, proximal barrel portion 73 is positioned within channel 190 of stabilizer 20 (refer to FIG. 8A-B). Cam wheel lock element 75 functions to lock the cam wheel 42 (not shown) preventing any inadvertent radial expansion of the distal sections 32 of the electrodes to a different radial state while protected by sleeve 21. When the thumb slide 41 is moved distally to advance the sleeve 21 over the distal sections 32 of the electrodes, cam wheel lock element 75 of rotational lock component 72 moves longitudinally to become seated within the cavity of cam wheel 42 (see FIG. 7). Because rotational lock component 72 is prevented from rotational movement along its longitudinal axis, the cam wheel lock 75 becomes immobilized and cannot be rotated. The lock 72 is prevented from any rotational movement by post section which is inserted through into bearing block 52. Bearing lock 52 includes openings through which the proximal segment of the electrodes are positioned and a single square central opening for receiving post section of rotational lock component 72. Referring again to FIG. 7, bearing block 52 is positioned within and permanently mounted to handle 68 by tabs 51. Bearing block component 52 thus functions to prevent rotation of the rotational lock component as well as providing a mounting area for the proximal ends 34 of the of electrodes. For completeness, upper extending prongs 193 of the retractor 430 are also shown in FIG. 9.

Figure 10:
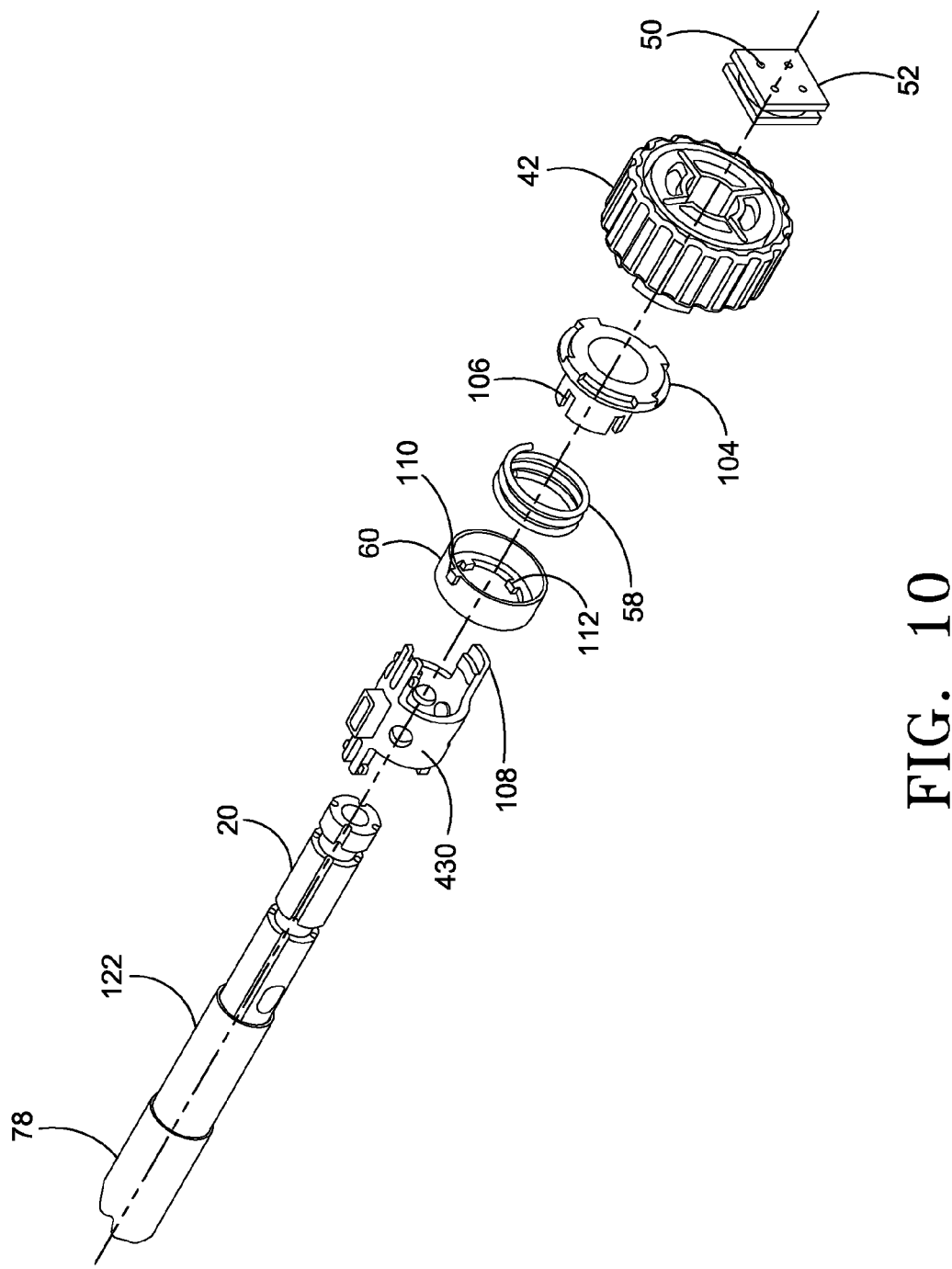
FIG. 10 is an exploded isometric view of components of an alternative embodiment of the slide mechanism of FIG. 9 showing the slide mechanism of the therapeutic energy delivery device of FIG. 1A controlling the position of the sleeve.
Figure 11:
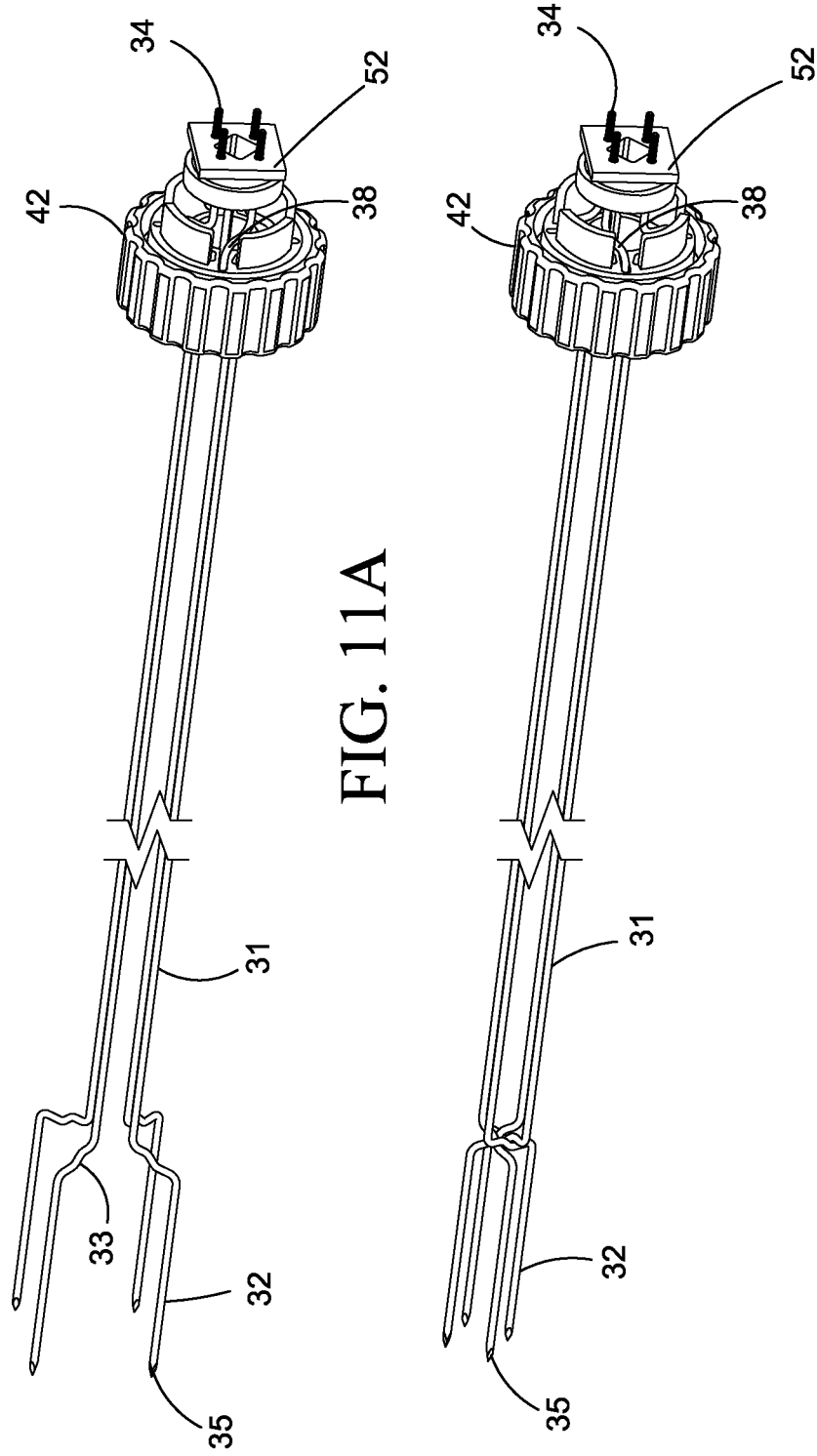
FIG. 11A is an isometric view of the rotational subassembly and electrodes expanded to a configuration where the distance between the distal section of any two electrodes is greatest.
FIG. 11B isometric view of the rotating cam subassembly with electrodes showing the rotational cam and the electrodes in a configuration where the distance between the distal section of any two electrodes is smallest.
Figure 12:
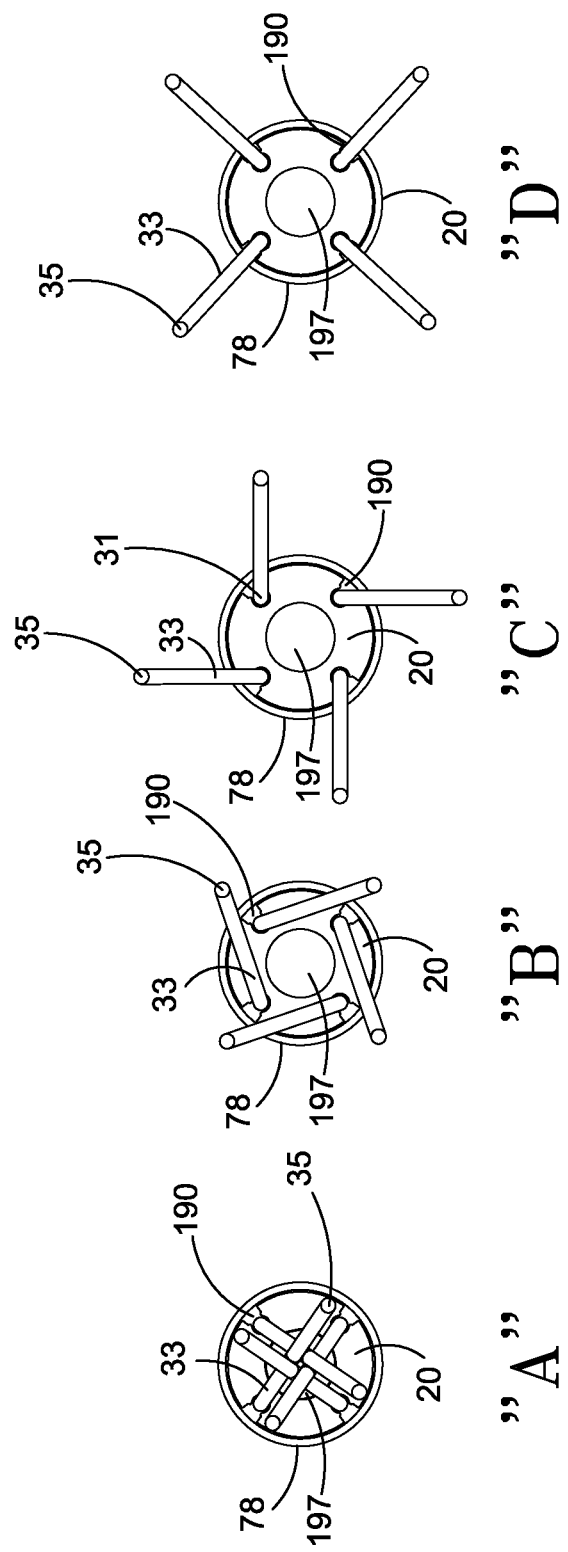
FIGS. 12A-D are distal end views of the therapeutic device 10 showing respectively the position of the electrodes as the electrodes are moved from a configuration where the distance between the distal section of any two electrodes is smallest (12A) to the configuration where the between the distal section of any two electrodes is greatest (12D). Two intermediate positions (FIGS. 12B-C) are also shown.

FIG. 10 is an exploded isometric view of components of an alternative embodiment of the slide mechanism of FIG. 9 that control the movement of sleeve 21, as well as locking the cam 42 while in position so as to prevent any inadvertent radial expansion of the electrode group while covered by sleeve 21. This embodiment differs from FIG. 9 in that there is an additional part called a rotational cam insert 104, and the lock sleeve has been altered such that there is not a lock pin 62 but rather a distal lock sleeve tab 110. When the slide is in its most distal position so as to cover the distal sections 32 of the electrodes, the lock sleeve 60 moves forward and the distal lock sleeve tabs 110 slide into a section of handle 68 (not shown). When this occurs, rotation of the distal sections 32 of the electrodes is prevented. To more clearly understand the interrelation of the parts, the following description is provided to show how the parts must fit together in an assembly: the slide 41 moves the lower extending prongs 108 of the retractor into contact with the lock sleeve 60, which presses against the spring 58 that then contacts the rotational cam insert 104. The lock sleeve tabs 112 interlock with the rotational cam insert grooves 106 of the rotational cam insert 104.

The spring 58 fits inside of the inner diameter of the lock sleeve 60. In certain embodiments additional protective coverings can be placed on the exterior of the elongated shaft 20 and FIG. 10 shows a protective covering 122. When the slide 41 is in a distal position to cover the distal sections 32 of the electrodes, the spring 58 is in its relaxed position. When the slide 41 moves proximally, the distal lock sleeve tab 110 slides out of the handle part that it fits within (not shown) and releases such that the distal sections 32 of the electrodes can be changed to an altered radial state via movement of the rotational cam 42.

FIG. 11A is an isometric view of the rotating cam subassembly with electrodes showing the rotational cam and the electrodes in a configuration where the distance between the distal section of any two electrodes is greatest (FIG. 11A), and FIG. 11B is an isometric view of the rotational cam showing the electrodes in a configuration where the distance between the distal section of any two electrodes is smallest. FIGS. 11A-11B show the rotating collar 42, the proximal section 31 of the electrodes, the distal section of the electrode 32, the proximal ends 34 of the electrodes, and the supporting member 52. FIG. 11A also designates the intermediate sections 33 of the electrodes. When the rotating collar 42 is turned, the proximal electrode section 31 turns and this alters the radial state of the distal section 32 of the electrodes. FIGS. 6A-C show that there is a U-shaped section of the proximal section 31 of the electrode that actually turns within slots 45 as the rotational cam 42 is turned, but this is no s in FIGS.11A-B.

FIGS. 12A-D are distal end views of the therapeutic energy delivery device 10 showing respectively the position of the electrodes as the electrodes are moved from a minimum outer diameter configuration to a maximum outer diameter configuration. For clarity, only the trocar 78, stabilizer 20 and electrodes 74 are shown.

FIG. 12A illustrates the electrodes positioned such that the outer diameter of the combined electrode group is smaller than the outer diameter of stabilizer 20 as well as the inner diameter of trocar 78. In one embodiment the outer diameter of the electrode group in its minimum configuration is approximately 0.35". In this minimum diameter position, protective sleeve 21 which has an inner diameter of approximately 0.395" may be advanced over the distal ends 35 into a protective position as shown in FIG. 1B. The sleeve 21 may also be retracted to expose the electrode group as shown in FIG. 2B. For completeness, the distance between any two adjacent electrodes in FIG. 12A to FIG. 12D respectively is 0.208, 0.326, 0.453, and 0.618 inches. In other words the distance between each electrode in FIG. 12A is 0.208 inches, and between each electrode in FIG. 12B is 0.326 inches, showing that electrodes are in their most compact state in FIG. 12A. For perspective, the channel 197 in stabilizer is also shown as is the electrode channel 190 in stabilizer.

To expand the initial outer diameter of the combined electrode group, cam wheel 42 is rotated counterclockwise. This action moves the U-shaped section 38 of each electrode (see FIG. 6A) in the direction of the cam rotation, which in turn causes each electrode to rotate on its own axis. As a result of this rotation, the intermediate section 33 of each electrode pivots outwardly from the central axis of the device as shown in FIG. 12B. In one embodiment, the electrodes pivot between 45-90° with an outer electrode group diameter of approximately of 0.50". Further rotation of cam 42 causes the electrodes to move to yet a larger overall diameter of approximately 0.71" as shown in FIG. 12C. At its largest diameter, shown in FIG. 12D, each electrode has rotated approximately 180° from its original minimum diameter position. In the embodiment shown, the maximum outer diameter of the electrode group is approximately 1 inch.

In a key aspect of the invention, therapeutic device 10 having a minimum diameter may be inserted into a patient through a laparoscopic device or other access means. The minimum outer diameter configuration may represent an operable treatment diameter for smaller ablation zones. Alternatively, for a larger ablation zone, the electrodes may be rotated outwardly using the cam wheel to provide a larger electrode group diameter. Thus, the invention described herein provides the operator with the ability to customize the overall diameter of the electrode group to correspond with the desired ablation volume. The device may also be used as a combination resection/ablation device. As an example, the operator position the device at a maximum diameter to ablate a 2-4 cm. tumor and then adjust the device to a minimum diameter to thermally coagulate a line of tissue in preparation for liver resection.

Figure 13A:
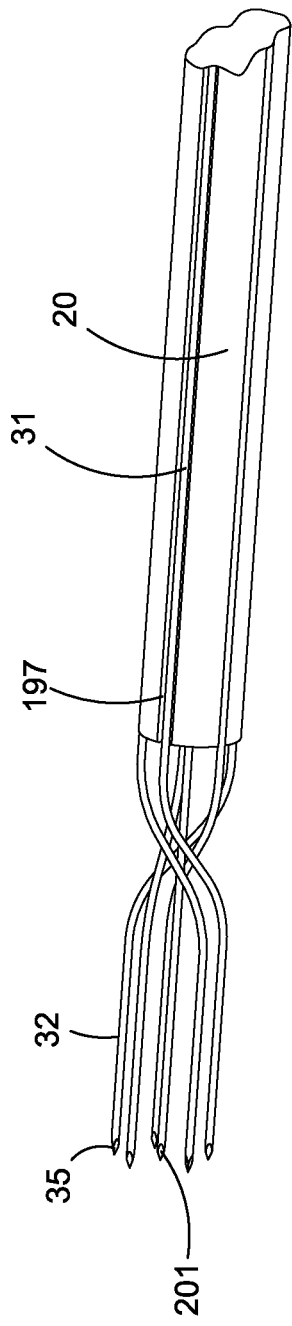
FIGS. 13A-13B are partial isometric views of the therapeutic energy delivery device showing a stabilizer and electrodes for an alternative embodiment of the device having six electrodes.
Figure 13B:
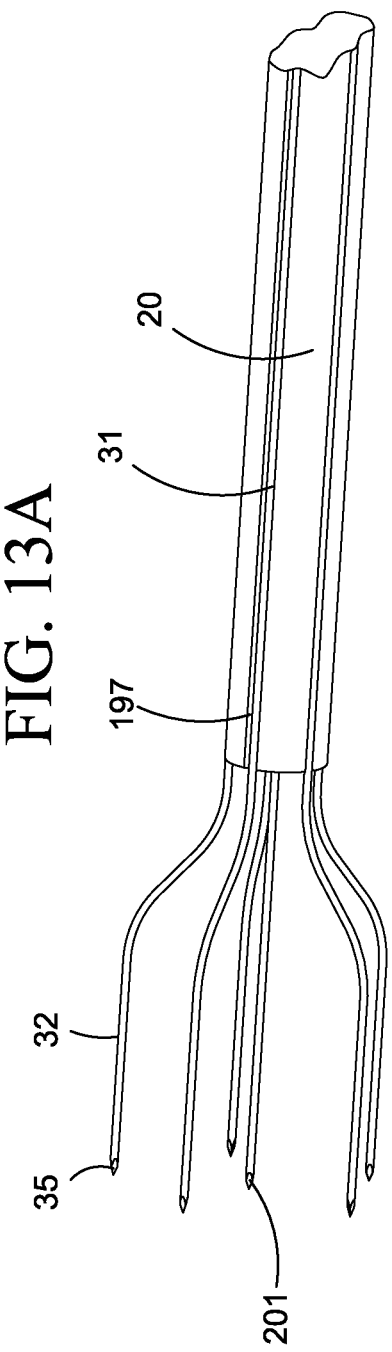
Figure 14:
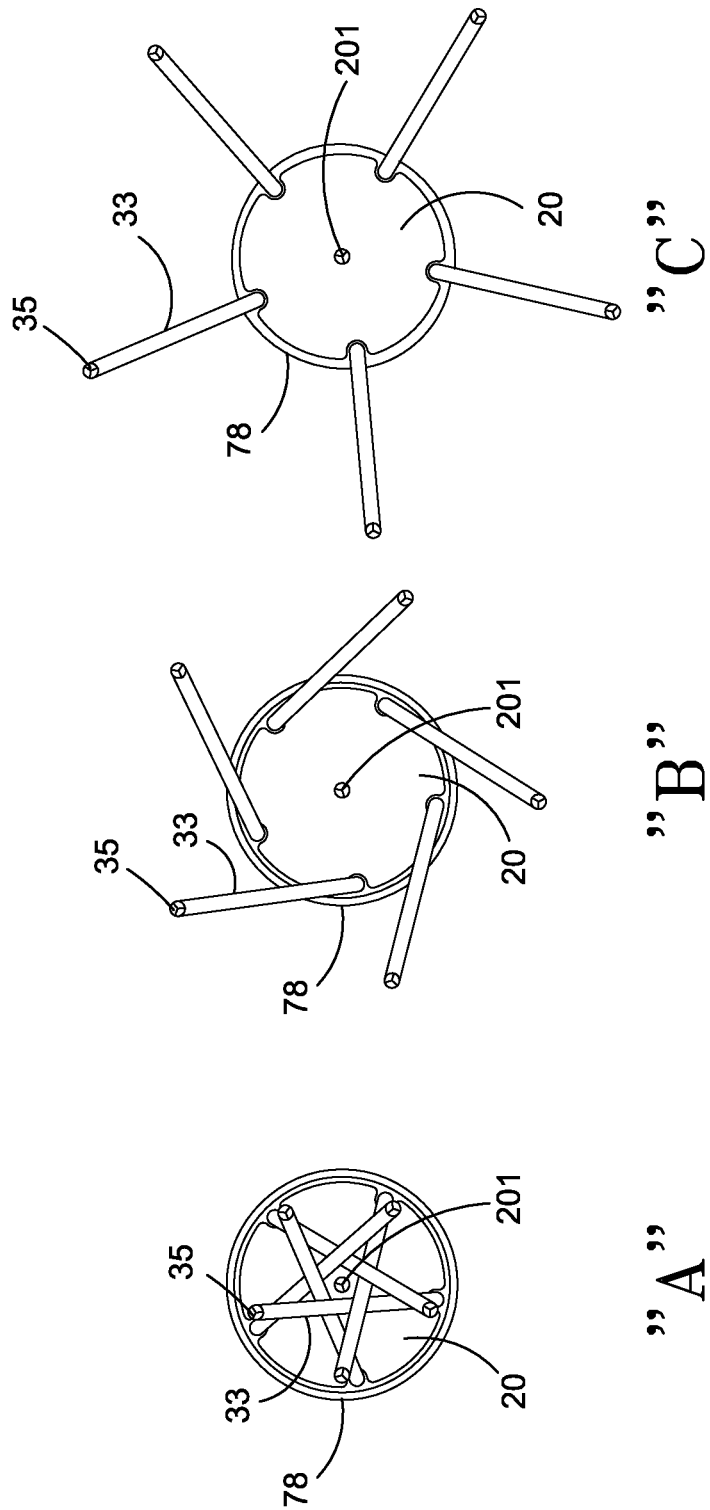
FIGS. 14A-C are distal end views of the therapeutic energy delivery device of FIG. 13A-B having six electrodes showing respectively the position of the electrodes as the electrodes are moved from a configuration where the distance between the distal section of any two electrodes is smallest (FIG. 14A) to a configuration where the distance between the distal section of any two electrodes is greatest (FIG. 14C). An intermediate configuration (FIG. 14B) is also shown.

FIGS. 13A-13B are partial isometric views of the therapeutic energy delivery device showing a stabilizer and electrodes for an alternative embodiment of the device having six electrodes. FIG. 13A shows the electrodes in shows the electrodes in a configuration where the distance between the distal sections of any two electrodes is smallest and FIG. 13B shows the electrodes in a configuration where the distance between the distal sections of any two electrodes is greatest. Shown are the distal sections 32 of the electrodes and the tip of each electrode 35, as well as the stabilizer 20. In this embodiment the distal section 32 of a central electrode 201 is also shown. Electrode 201 is aligned with the central axis of the device and does not rotate in response to the rotation of the cam wheel. Having a central electrode allows for larger ablation volumes by providing for more optimal coverage of ablation areas through more equal spacing of the electrodes for complete ablation coverage of a targeted region.

FIGS. 14A-C illustrate distal end views of the therapeutic energy delivery device 10 of FIG. 13 having a six-electrode configuration and showing respectively the position of the electrodes as the electrodes are moved from a minimum outer diameter configuration to a maximum outer diameter configuration. For clarity, only the trocar 78, stabilizer 20 and electrodes 74 are shown. FIG. 14A illustrates the electrodes positioned such that the outer diameter of the combined electrode group is smaller than the outer diameter of stabilizer 20 as well as the inner diameter of trocar 78. Central, non-rotating electrode 201 is positioned on the center longitudinal axis of the stabilizer and does not include any bends. The intermediate sections of the remaining electrodes are positioned in an overlapping relationship forming star-like configuration. In one embodiment the outer diameter of the electrode group in its minimum configuration is approximately 0.35". To expand the initial outer diameter of the combined electrode group, cam wheel 42 is rotated counterclockwise. This action moves the U-shaped section 38 of each electrode (see FIG. 6A) in the direction of the cam rotation, which in turn causes each electrode to rotate on its own axis. As a result of this rotation, the intermediate section 33 of each electrode pivots outwardly from the central axis approximately 45° Further rotation of cam 42 causes the electrodes to move to yet a larger overall diameter which extends radially outward from the outer diameter of the stabilizer 20 and trocar 78. At its largest diameter, shown in FIG. 14C, each electrode has rotated approximately 160° from its original minimum diameter position. For the six-electrode model, certain embodiments involve a largest radial state with: an ablation diameter of up to 45 millimeters, with a distance from the distal section 32 of the center electrode to the distal section of a non-center electrode being 18 millimeters, and with the distance between any two non-central electrodes being 22 millimeters. In certain embodiments a 15 millimeter length trocar is used. These particular embodiments contrast with the 4 electrode model, where the trocar can be 10 millimeters in diameter, there can be in certain embodiments up to a 3 cm ablation diameter, adjacent electrodes can be up to 17 millimeters apart, and diagonal electrodes can be spaced up to 24 millimeters apart. Also, in certain embodiments a 5-electrode model can be used, wherein there is a central electrode with four surrounding electrodes; in that model the trocar can be 12 millimeters long, there can be up to a 36 millimeter ablation, each adjacent electrode can be 20 millimeters apart, and the non-central electrodes can be spaced diagonally apart up to 24 millimeters. Having a central electrode allows for larger ablation volumes by providing for more optimal coverage of ablation areas through more equal spacing of the electrodes for complete ablation coverage of a targeted region.

Figure 15:
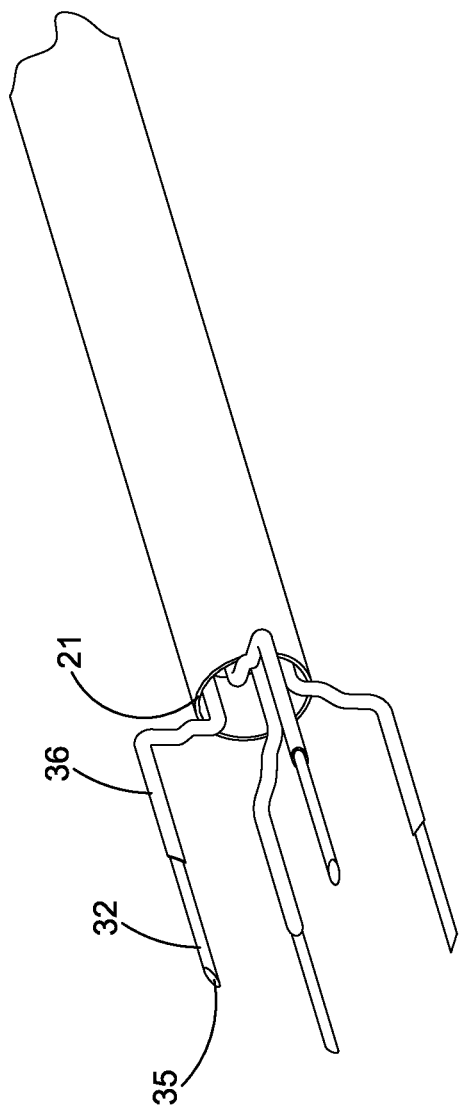
FIG. 15 is an partial isometric view of the distal segment of an alternative embodiment of the therapeutic energy delivery device having four electrodes having insulation placed through tubes wherein a mechanism at the proximal end of the device can be used to move the electrodes proximally and distally within the tubes. In addition, the insulation can be slid proximally and distally to ensure that electrodes coming in close contact are electrically separated; the insulation can extend to the end of the intermediate section 33 of the electrodes and in certain embodiments can extend into at least a portion of the distal section 32 of the electrodes. Insulation extends in a distal direction to encompass the intermediate sections 33 of the electrodes to prevent cross-conductivity of electrodes in close proximity. The insulation can be made slideable through a controller at the proximal end of the device.

FIG. 15 is an isometric view of the distal end of an alternative embodiment of the therapeutic energy delivery device having four electrodes placed through tubes wherein the length of the exposed electrode can be set. Shown are the distal sections 32 of the electrodes, the tip 35 of each electrode, tubes 36 through which the electrodes can be placed, and the sleeve 21. In this embodiment the electrodes are inserted through tubes 36 such that the distal sections 32 of the electrodes extend in a distal direction from the tubes 36. The insulation can also be moved proximally or distally and will extend distally beyond the intermediate sections 33 of the electrodes to protect the electrodes from touching. The tips of the tubes 36 are sharp and in certain embodiments can be placed through tissue prior to placing the electrodes through the end of the tubes. This embodiment is particularly useful for treating intra-mural tissue which is below a tissue surface. The surface of the tissue can first be pierced by the tips of the tubes 36, and then the amount of exposed electrode can be adjusted within the tissue. Alternatively, the tissue can be pierced by the electrodes themselves. In this embodiment, a set depth below the tissue surface can be achieved where the treatment energy does not extend all the way to the tissue surface. Such a device and method is particularly useful for treating the liver or other large organs, where intra-mural tissue treatment is required.

In another related embodiment, the tubes 36 can be connected to a slide mechanism 41 such that the amount of exposed electrode can be adjusted by controlling the position of the insulative tubes 36 relative to the electrodes which remain in a fixed position.

Figure 16:
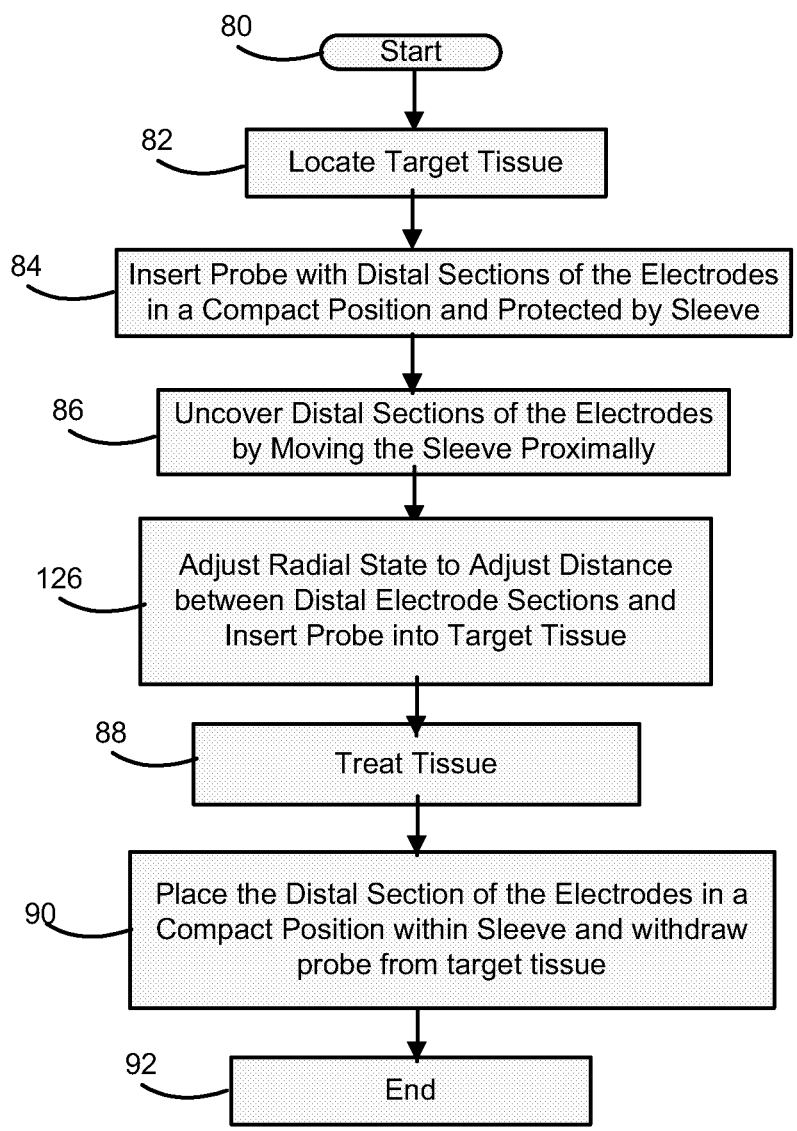
FIG. 16 is a flowchart illustrating a method of treatment using the therapeutic energy delivery device.

FIG. 16 is a flowchart illustrating a method of treatment using the therapeutic energy delivery device so as to ensure safety and provide for the option of placing the electrodes, that are in a configuration where the distance between the distal section of any two electrodes is smallest, covered with a protective sleeve to be inserted into a target area and then to uncover the distal section of the electrodes by moving the sleeve and treat the patient with electrodes placed in a configuration where the distance between the distal sections of any two electrodes is greatest. The procedure is started 80, the target tissue is located 82, and the probe is inserted 84 into the tissue with electrodes in a compact position and protected by the sleeve. The term probe here refers to the sections of the therapeutic energy delivery device distal to the most distal to the most distal section of the handle, and can include the electrodes sections capable of ablation and the portions of the stabilizer and trocar of the therapeutic energy delivery device distal to the most distal part of the handle. In certain cases a part of the probe will be inserted into the patient, and in various cases this will be performed through laparoscopy. In various embodiments the device can be used for treatment of a target region where the treatment is for irreversible electroporation and then the device can be withdrawn and energy applied for radiofrequency (RF) treatment so that track ablation can occur to prevent seeding and in various cases to cause coagulation. In other embodiments RF treatment can precede IRE treatment in a target region. The combination of IRE and RF treatment can be performed using multiple generators or a generator with software or controls to alter the settings. In other words a probe can be coupled to a first generator and, once the probe is placed into a target region, the target region can be treated with IRE. Subsequently the probe can be uncoupled from the first generator and coupled to a second generator meant for RF treatment and the treatment can continue, either on the target region or on a track as the probe is withdrawn so as to apply thermal treatment of the track. Or a single generator can be used where a mechanical or electrical switch was used to change from one setting to another so as to allow IRE treatment or RF treatment or both, in any combination through probe insertion, treatment, and withdrawal. The sleeve is moved to uncover the electrodes 86, the radial state is set 126 to adjust the distance between the distal electrode 32 sections the tissue is treated 88, and then the probe is placed in a compact configuration and the sleeve is used to cover the distal sections of the electrodes 90, and the procedure is ended 92. In certain cases the electrodes or device will be moved, replaced, or reinserted to perform more than one treatment or ablation as needed for therapeutic benefit, wherein the procedure is repeated.

Figure 17:
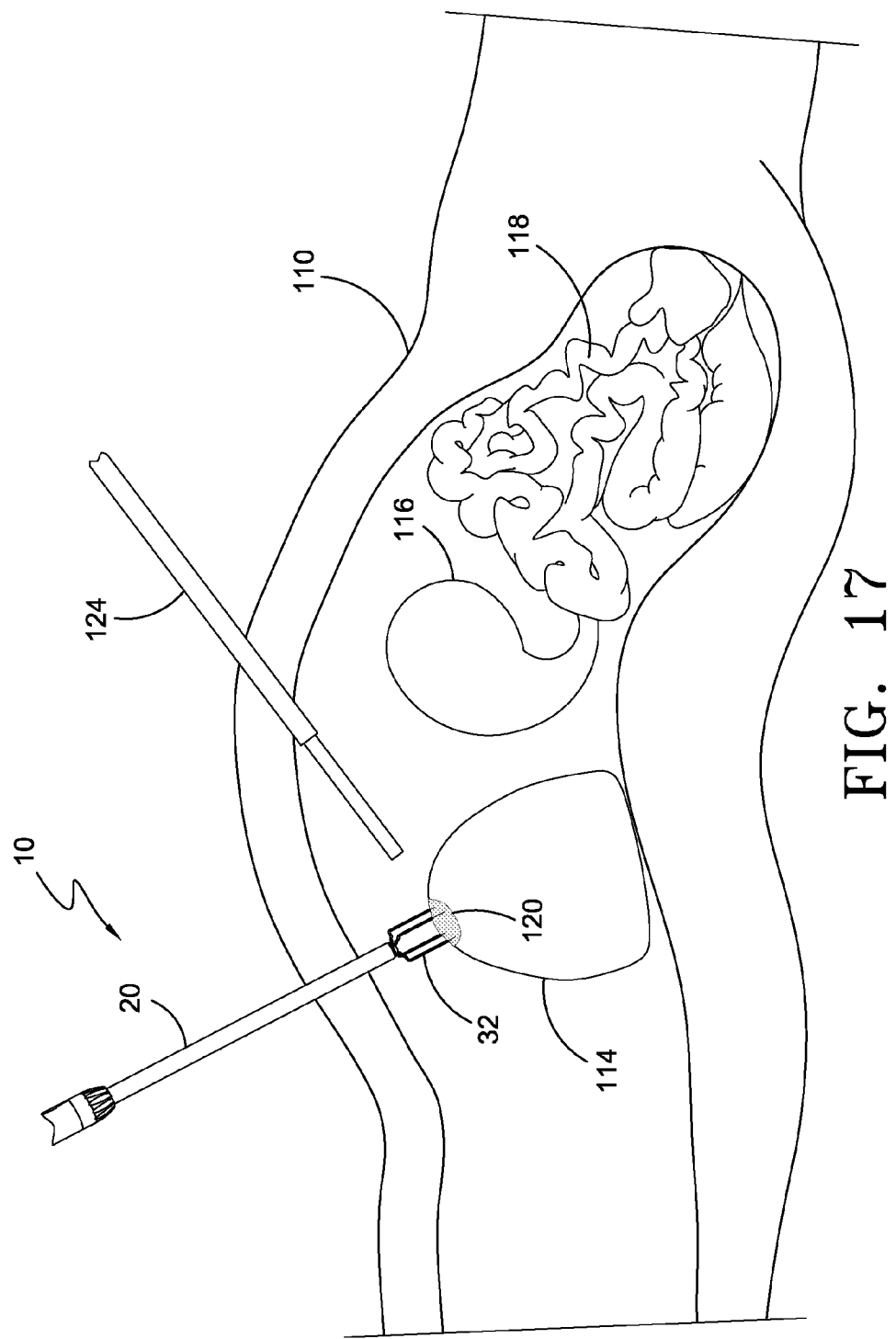
FIG. 17 is a partial cut-away view of the side of a patient torso depicting the method of treatment using the therapeutic energy delivery device to treat a liver tumor.

FIG. 17 is a partial cut-away view of the side of a patient torso depicting the method of treatment using the therapeutic energy delivery device to treat a liver tumor or other portion of undesirable tissue within a liver. Shown is the therapeutic device 10 where the elongated shaft 20 has been placed through the skin, fat, and muscle layers of the surface of the patient 110 and has been placed so that the distal sections 32 of the electrodes are touching a zone to be ablated 120 within a liver 114. For perspective also shown are a stomach 116, intestine 118, and visualization device 124. This figure shows how the device can be placed with precision within or adjacent to undesirable tissue and that the electrodes can be placed to the desired depth for ablation. The active electrode length can be altered by movement of slideable insulation (not shown), and the amount of ablation can be tailored not only by the active electrode length but by the radial state as well. Regarding the movement of the insulation, the section of the distal portion 32 of the electrodes that does not have an insulation covering is said to be the electrically exposed portion. This portion is electrically active. This length can be essentially any length up to the length of the distal sections 32 of the electrodes.

TED devices 10 of the present invention and components therein may be able to withstand exposure to 2× ethylene oxide sterilization without incurring functional failures. TED devices and components therein may be substantially biocompatible.

TED devices 10 disclosed herein may be used in monopolar configurations and/or bipolar configurations. The geometry of resulting ablation/resection volumes may depend at least in part on the configuration of the distal sections 32 of the electrodes. For example, with a linear arrangement of two or more electrodes, the ablation volume may have a minimum diameter of 1 mm to 2 mm, such as 1.8 mm. With a two-dimension arrangement of four or more electrodes, the ablation volume may have a major cross-section, at a minimum, of 5×5 mm to 10×10 mm, such as 8×8 mm. TED devices may be activated by switch through depression of switch actuator on the hand piece 40. Alternatively or in combination, TED devices may be activated by one or more foot pedals.

The combination of the sleeve 21 and the rotating device 42 allows the distal sections 32 of the electrodes to be initially inserted through a small opening (such as the lumen of a laparoscopic trocar) without the risk of damage to the distal sections 32. The device can also be inserted into a lumen of a laparoscope. Once the device 10 has been inserted through the opening (such as the lumen of the laparoscopic trocar), the sleeve 21 is moved and the distal sections 32 of the electrodes are exposed. The rotating device 42 is then rotated to cause the distal sections 32 of the electrodes to move radially outward. Preferably, as the distal sections 32 of the electrodes are rotated so that the distance between the distal sections of any two electrodes becomes greater, the distal sections 32 of the electrodes are moved radially outward at least to a point outside the perimeter of the elongated shaft 20. The amount of radial movement of the distal sections 32 of the electrodes is controlled by the amount of rotation of the rotating collar 42. Such degree of freedom allows an operator to position the distal sections 32 of the electrodes of the device 10 into predetermined target tissues during use. Therefore, the size of the treatment area being defined by the distal sections of the electrodes is controlled by the amount of rotation of the rotating collar 42. This minimizes the need for repeated treatment.

Software on a computer-readable medium may be used to control certain aspects of using the devices, such as controlling power (e.g., amplitude, pulse frequency) to the device, analyzing feedback signals from electrodes (e.g., thermal readings, impedance, visual signals), and providing signals for actions (e.g., readiness, stand-by, power-on, power-off, warnings, failure signals). For example, a software package stored or installed on a computer-readable medium may be used for facilitating and/or enabling the methods and/or processes of using the TED devices 10. The device can be coupled to software enabling capturing data from the distal sections 32 of the electrodes such that there are feedback loops such that the software can visually demonstrate (or additionally through audio) to the user that the treatment is proceeding as planned or that there are difficulties or errors in the treatment or in the orientation or configuration of the electrodes or the position of the device. The user can use the feedback to change the treatment including the orientation of the probe, the position of the probe, the electrode configuration or orientation, the exposed electrodes, the active electrode, the insulation position, or other features to ensure proper treatment.

Methods and processes of using the devices disclosed herein may involve one, two, or more of the following actions: at least a portion of the therapeutic device 10 is inserted into a body cavity, rotating the plurality of electrodes thereby causing the distal sections to move radially outward, positioning the distal sections near the tissue, and delivering therapeutic energy through the electrodes to treat the tissue. The therapeutic device 10 has a housing 40 having a surface. The therapeutic device 10 has a plurality of electrodes 74, wherein each electrode includes: (i) a proximal section 31 longitudinally extending from the housing 40 and having a longitudinal axis; (ii) an intermediate section 33 extending from the proximal section 31; and (iii) a distal section 32 extending longitudinally from the intermediate section 33. The plurality of electrodes are rotated thereby causing the distal sections 32 to move radially outward relative to the elongated shaft 20. The distal sections 32 can be positioned in the tissue. Therapeutic energy can be delivered through the electrodes to treat the tissue. In one embodiment of the method, the tissue that is treated is pancreatic cancer tissue. The method can be carried out during a laparoscopic procedure, wherein the therapeutic device 10 is inserted into a lumen of a laparoscopic trocar. In various embodiments the treated tissue can be physiologically normal or tissue of a pathology, and can include tumors or cancers. Treatment can involve normal organ systems or parts of organ systems including digestive, skeletal, muscular, nervous, endocrine, circulatory, reproductive, integumentary, lymphatic, urinary tissue or organs, or other soft tissue or organs where selective ablation is desired.

The method results in at least one resection, excision, coagulation, disruption, denaturation, or ablation of the target tissue. The method can be used for laparoscopic coagulation prior to tissue resection as is commonly known in liver surgeries. Following the treatment and before removing the device from the body, the rotating device can be rotated in a direction to cause the distal sections of the electrodes 32 to move radially inward towards the center of the elongated shaft 20. Sleeve 21 may be moved to cover and protect the distal sections 32 of the electrodes. Treatment device 10 may then be safely removed from the patient without causing unintended effects.

This device can be used to ablate tissue or coagulate tissue for resection, or be used for a combination of these functions. The device can be used to tailor the type or size of the area to be treated. The tips of the electrodes can be used to deliver voltage or the entire length of the distal section of the electrodes can be used. In addition, the radial state of the distal electrode section of the current device can be set to ensure ablation to match the size of the targeted area, so that one device can be used for treatment of multiple conditions and target tissues whereas previously multiple devices would have been necessary. The device can be used to coagulate tissue, thus preventing bleeding. The parameters can be changed manually or electronically to move from an ablation setting to parameters such that bleeding is controlled; this can be changed either through use of software or by the manual actions of the probe user. The device can also be used for coagulation for resection and this function can be performed through use of the probe at any radial state of the distal sections 32 of the electrodes.

TED devices disclosed herein are designed for tissue destruction in general, such as resection, excision, coagulation, disruption, denaturation, and ablation, and are applicable in a variety of surgical procedures, including but not limited to open surgeries, minimally invasive surgeries (e.g., laparoscopic surgeries, endoscopic surgeries, surgeries through natural body orifices), thermal ablation surgeries, non-thermal surgeries, as well as other procedures known to one of ordinary skill in the art. The devices may be designed as disposables or for repeated uses.

In certain embodiments the elongated shaft 20 can involve an articulating region that can allow a greater range of motion. The articulating region may include a hinge which allows for the distal section of the elongated shaft to articulate or bend with respect to the longitudinal axis of the shaft. (An articulating probe is described in patent application Ser. No. 12/26730, Articulatable Device for Delivering Therapeutic Energy to Tissue, filed Nov. 7, 2008, herein incorporated by reference.) This allows for insertion of The distal electrodes 32 into a body, and allows for a range of motion so that difficult areas can be reached. The articulation can include a single area of articulation or multiple areas of articulation and can be controlled via any mechanism known in the art from a device coupled to the handle housing 40. In certain embodiments the angle of articulation of the distal portion of the probe is 30 degrees to 90 degrees relative to the longitudinal axis of the device.

In various embodiments a portion of the proximal sections 31 of the electrodes at the point of the rotational cam are placed very close together so that in certain embodiment the electrodes are separated only by insulation when at the point of the bearing block 52. In such embodiments there is no U-shape 38 section of the proximal section 32 of the electrode. Instead when moving from the proximal ends 34 of the electrodes distally along the proximal section 31 of the electrodes, the electrodes 74 angle away from each other. In certain embodiments the proximal electrodes become parallel to each other proximal to the intermediate sections 33 of the electrodes. Such embodiments allow easier assembly. The elongated shaft 20 is not necessary in such models as the electrodes rotate together along the center axis of the trocar (or along the center axis of the center electrode in embodiments having a center electrode). This is in contrast to having each electrode rotate around its own axis as is the case in certain embodiments.

In certain embodiments of those mentioned above, where a portion of the proximal sections 31 of the electrodes at the point of the rotational cam are placed very close together so that in certain embodiment the electrodes are separated only by insulation when at the point of the bearing block 52, there are no slots 45 within the rotating collar (clearly depicted in FIGS. 6A-C); rather, these slots have been replaced by holes through which at least a portion of the proximal sections 31 of the electrodes are positioned such that the electrodes can rotate as a group in a small diameter. The electrodes do not slide back and forth within the slots but rather rotate and do so as a group. The holes can be dimensioned substantially the same diameter as the electrodes but so as to allow rotation. The holes can also be cut so that they are angled so as to accept non-parallel electrodes as they angle out from proximal to distal moving away from bearing block 52.

As indicated, in certain embodiments IRE treatment Will be utilized. More particularly, in one aspect, the total number of pulses and pulse trains in various embodiments can be varied based on the desired treatment outcome and the effectiveness of the treatment for a given tissue. During delivery of non-thermal IRE energy to target tissue, a voltage can be generated that is configured to successfully, ablate tissue. In one aspect, certain embodiments can involve pulses between about 5 microseconds and about 62,000 milliseconds, while others can involve pulses of about 75 microseconds and about 20,000 milliseconds. In yet another embodiment, the ablation pulse applied to the target tissue can be between about 20 microseconds and 100 microseconds. In one aspect, the at least one energy source can be configured to release at least one pulse of energy for between about 100 microseconds to about 100 seconds and can be adjustable at 10 microsecond intervals. In certain embodiments the electrodes described herein can provide a voltage of about 100 volts per centimeter (V/cm) to about 7,000 V/cm to the target tissue. In other exemplary embodiments, the voltage can be about 200 V/cm to about 2000 V/cm as well as from about 300 V/cm to about 1000 V/cm. Other exemplary embodiments can involve voltages of about 2,000 V/cm to about 20,000 V/cm. In one exemplary aspect, the bipolar probe can be used at a voltage of up to about 2700 volts. As indicated, in various embodiments IRE treatment can be used in conjunction with reversible electroporation or other thermal treatments such as RE In one exemplary embodiment thermal energy can be applied such that it produces fluctuations in temperature to effect treatment. In one aspect, the thermal energy provided to the tissue can heat the target tissue to between about 50° C. and about 105° C. to bring about cell death. In one aspect the temperature can be adjusted such that it can be lesser or greater than this temperature range, depending on the exact rate of speed of removal of the energy delivery device from the target tissue In one embodiment the temperature used is between about 105° C. and about 110° C., although one of ordinary skill would recognize that temperatures above about 105° C. can cause tissue vaporization.

The above disclosure is intended to be illustrative and not exhaustive. This description will suggest many modifications, variations, and alternatives may be made by ordinary skill in this art without departing from the scope of the invention. Those familiar with the art may recognize other equivalents to the specific embodiments described herein. Accordingly, the scope of the invention is not limited to the foregoing specification.

What is claimed is:

1. A device for delivering therapeutic energy to tissue, comprising:
    a housing;
    a plurality of electrodes, each electrode including:
        a proximal section longitudinally extending from within the housing and having a longitudinal axis;
        an intermediate section extending from the proximal section;
        a distal section extending longitudinally from the intermediate section;
    a rotating device coupled to the proximal sections of the plurality of electrodes and adapted to rotate the plurality of electrodes by rotating the proximal section of each electrode about its longitudinal axis to move the distal sections of the electrodes from a first radial state to a second radial state; and
    wherein in the first radial state, at least a portion of the intermediate section of at least one electrode overlaps at least a portion of the intermediate section of an adjacent electrode.

2. The device of claim 1, wherein the distal sections of the electrodes are arranged substantially parallel to each other.

3. The device of claim , wherein the distal sections of the electrodes are uniformly spaced from each other.

4. The device of claim 1, wherein the intermediate section includes at least one bend to allow at least a portion of the electrodes to overlap each other when in the first radial state.

5. The device of claim 1, wherein the intermediate sections of the plurality of electrodes extend in a generally radial direction, and wherein the intermediate sections and distal sections of each electrode together form a generally L-shaped configuration.

6. The device of claim 1, wherein the proximal section has a proximal end and a distal end, and wherein each proximal section of the electrode includes a "U-shaped" section positioned at the proximal end.

7. The device of claim 1, wherein the plurality of electrodes is selected from a group consisting of: four and six electrodes.

8. The device of claim 7, wherein at least a portion of at least one of the plurality of electrodes is surrounded by an insulation layer.

9. A device for delivering therapeutic energy to tissue, comprising:
    a housing;
    a plurality of electrodes, each electrode including:
        a proximal section longitudinally extending from within the housing and having a longitudinal axis;

an intermediate section extending from the proximal section;
a distal section extending longitudinally from the intermediate section;
a rotating device coupled to the proximal sections of the plurality of electrodes and adapted to rotate the plurality of electrodes about their respective longitudinal axes to move the distal sections of the electrodes radially outwardly relative to the outer surface of the housing from a first radial state to a second radial state to define a treatment zone;
an elongated shaft having a proximal end, a distal end, an outer surface, and a longitudinal axis, the proximal end of the elongated shaft is coupled to at least a portion of the housing, at least a portion of the plurality of electrodes extends longitudinally within the elongate shaft; and
at least one electrode of the plurality electrodes is aligned with the longitudinal axis of the elongated shaft.

10. The device of claim 9, wherein:
the plurality of electrodes in the first radial state are sized to be received within at least a portion of a lumen of a laparoscope; and
the distal sections of the electrodes are in substantially parallel arrangement during rotation of the plurality of the electrodes by the rotating device.

11. The device of claim 9, wherein when the rotating device is rotated, the distal section moves from the first radial state radially outward to the second radial state, the second radial state having a radius that is larger than a radius of the shaft.

12. The device of claim 11, wherein the rotating device is a rotating collar, and wherein the rotating collar is coupled to the housing and the proximal sections of the plurality of the electrodes.

13. The device of claim 9, further comprising a sleeve, wherein the sleeve can be moved and wherein the sleeve surrounds at least a portion of and is slidably disposed around at least a portion of the outer surface of the shaft.

14. The device of claim 13, further comprising a slide, wherein the slide is coupled to the sleeve, wherein when the slide is moved from a first position to a second position, the sleeve substantially surrounds at least one electrode of the plurality of electrodes, such that the plurality of electrodes is locked in position.

* * * * *